(12) United States Patent
Rabiner et al.

(10) Patent No.: US 7,494,468 B2
(45) Date of Patent: *Feb. 24, 2009

(54) ULTRASONIC MEDICAL DEVICE OPERATING IN A TRANSVERSE MODE

(75) Inventors: Robert A. Rabiner, Chelmsford, MA (US); Bradley A. Hare, Chelmsford, MA (US); David M. Fischer, Waltham, MA (US); Andy Levine, Newton Centre, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 504 days.

This patent is subject to a terminal disclaimer.

(21) Appl. No.: 10/371,781

(22) Filed: Feb. 21, 2003

(65) Prior Publication Data

US 2003/0125645 A1  Jul. 3, 2003

Related U.S. Application Data

(63) Continuation of application No. 09/618,352, filed on Jul. 19, 2000, now Pat. No. 6,551,337.

(60) Provisional application No. 60/178,901, filed on Jan. 28, 2000, provisional application No. 60/157,824, filed on Oct. 5, 1999.

(51) Int. Cl.
*A61B 8/00* (2006.01)
*A61B 17/32* (2006.01)

(52) U.S. Cl. .................. 600/459; 600/437; 606/169

(58) Field of Classification Search ............. 606/159, 606/167, 169, 170, 171; 601/2; 604/22; 600/437, 439, 459, 462
See application file for complete search history.

(56) References Cited

U.S. PATENT DOCUMENTS 168,975 A  10/1875  Farmer (Continued)

FOREIGN PATENT DOCUMENTS

CA  2251096  8/1998

(Continued)

OTHER PUBLICATIONS

European Search Report for application No. EP04024818 dated Dec. 22, 2004.

(Continued)

*Primary Examiner*—Long V Le
*Assistant Examiner*—Jacqueline Cheng
(74) *Attorney, Agent, or Firm*—Fish & Richardson P.C.

(57) ABSTRACT

An ultrasonic medical device comprises an ultrasonic vibration generator that generates vibration along its longitudinal axis. The ultrasonic vibration is transmitted through an ultrasonic coupler and a series of transformer sections that amplify the ultrasonic vibration. A flexible member is coupled to the distal end of the transformer sections, and is thus supplied with a longitudinal vibration at its base by the transformer sections. The flexible member is designed so that it converts the longitudinal vibration into a standing wave that runs along the length of the flexible member. The standing wave produces a series of nodes and anti-nodes along the length of the flexible member. Each of the anti-nodes produces cavitation in fluids in contact with the probe. The cavitation of the fluids causes destruction of adjacent tissue. In this manner, the entire length of the flexible member becomes a working surface that may be utilized for destroying tissue.

50 Claims, 4 Drawing Sheets

U.S. PATENT DOCUMENTS

| | | | |
|---|---|---|---|
| 323,762 A | 8/1885 | White | |
| 404,319 A | 5/1889 | Taylor | |
| 414,090 A | 10/1889 | Taylor | |
| 1,045,326 A | 11/1912 | Ruflin | |
| 1,239,451 A | 9/1917 | Belz | |
| 1,779,478 A | 10/1930 | Leech | |
| 1,861,769 A | 6/1932 | Wappler | |
| 2,199,602 A | 5/1940 | Wright | |
| 2,242,120 A | 5/1941 | Gardiner | |
| 2,270,922 A | 1/1942 | Bechmann et al. | |
| 2,321,358 A | 6/1943 | Bokovoy | |
| 2,514,080 A | 7/1950 | Mason | |
| 2,742,076 A | 4/1956 | Klein | |
| 2,838,695 A | 6/1958 | Thurston | |
| 2,843,176 A | 6/1958 | Franck | |
| 2,917,691 A | 12/1959 | De Prisco et al. | |
| 2,990,616 A | 7/1961 | Balamuth et al. | 433/119 |
| 3,056,698 A | 10/1962 | Kleesattel et al. | |
| 3,089,790 A | 5/1963 | Balamuth et al. | |
| 3,113,225 A | 12/1963 | Kleesattel et al. | |
| 3,132,548 A | 5/1964 | Livermont | |
| 3,133,351 A | 5/1964 | von Seggern | |
| 3,202,021 A | 8/1965 | Livermont | |
| 3,229,523 A * | 1/1966 | Boyd et al. | 73/290 V |
| 3,241,780 A | 3/1966 | Kitselman | |
| 3,304,449 A | 2/1967 | Pohlman et al. | |
| 3,315,663 A | 4/1967 | Goldfarb | |
| 3,401,446 A | 9/1968 | Obeda et al. | |
| 3,433,226 A | 3/1969 | Boyd | |
| 3,438,824 A | 4/1969 | Balamuth | |
| 3,486,361 A | 12/1969 | Vaneman et al. | |
| 3,524,085 A | 8/1970 | Shoh | |
| 3,526,219 A | 9/1970 | Balamuth | 600/565 |
| 3,528,410 A | 9/1970 | Banko | |
| 3,565,062 A | 2/1971 | Kuris | 606/169 |
| 3,589,363 A | 6/1971 | Banko | 604/22 |
| 3,614,484 A | 10/1971 | Shoh | |
| 3,660,186 A | 5/1972 | Sager et al. | |
| 3,683,736 A | 8/1972 | Loose | |
| 3,763,680 A | 10/1973 | Godfrey et al. | |
| 3,805,787 A | 4/1974 | Banko | 604/22 |
| 3,809,977 A | 5/1974 | Balamuth et al. | |
| 3,840,932 A | 10/1974 | Balamuth et al. | |
| 3,853,130 A | 12/1974 | Sheridan | |
| 3,861,391 A | 1/1975 | Antonevich et al. | 606/128 |
| 3,890,977 A | 6/1975 | Wilson | |
| 3,906,954 A | 9/1975 | Baehr et al. | |
| 3,939,033 A | 2/1976 | Grgach et al. | |
| 3,955,662 A | 5/1976 | Thackston | |
| 3,962,898 A | 6/1976 | Tillmann | |
| 3,967,621 A | 7/1976 | Schwarz | |
| 3,980,906 A | 9/1976 | Kuris et al. | |
| 3,988,782 A | 11/1976 | Dardik et al. | |
| 3,990,452 A | 11/1976 | Murry et al. | |
| 3,991,929 A | 11/1976 | Smith | |
| 4,011,474 A | 3/1977 | O'Neill | |
| 4,012,174 A | 3/1977 | Seibel et al. | |
| 4,012,647 A | 3/1977 | Balamuth et al. | |
| 4,044,174 A | 8/1977 | Carr | |
| 4,063,557 A | 12/1977 | Wuchinich et al. | |
| 4,069,541 A | 1/1978 | Williams et al. | |
| 4,083,996 A | 4/1978 | Tanaka et al. | |
| 4,136,700 A | 1/1979 | Broadwin et al. | 606/169 |
| 4,143,130 A | 3/1979 | Imondi et al. | |
| 4,144,646 A | 3/1979 | Takemoto et al. | |
| 4,157,396 A | 6/1979 | Tanaka et al. | |
| 4,164,524 A | 8/1979 | Ward et al. | |
| 4,169,984 A | 10/1979 | Parisi | |
| 4,174,410 A | 11/1979 | Smith | |
| 4,178,935 A | 12/1979 | Gekhman et al. | |
| 4,203,429 A | 5/1980 | Vasilevsky et al. | |
| 4,203,444 A | 5/1980 | Bonnell et al. | |
| 4,223,676 A | 9/1980 | Wuchinich et al. | |
| 4,225,803 A | 9/1980 | Goof | |
| 4,236,510 A | 12/1980 | Hatter et al. | 601/2 |
| 4,248,232 A | 2/1981 | Engelbrecht et al. | |
| 4,265,928 A | 5/1981 | Braun | |
| 4,280,233 A | 7/1981 | Raab | |
| 4,300,564 A | 11/1981 | Furihata | |
| 4,311,147 A | 1/1982 | Hausler | |
| 4,315,181 A | 2/1982 | Holze, Jr. | |
| 4,316,465 A | 2/1982 | Dotson, Jr. | |
| 4,326,903 A | 4/1982 | Summo | |
| 4,334,168 A | 6/1982 | Besson et al. | |
| 4,335,426 A | 6/1982 | Maxwell et al. | |
| 4,352,570 A | 10/1982 | Firth | |
| 4,356,590 A | 11/1982 | Goldsmith | |
| 4,363,992 A | 12/1982 | Holze, Jr. | |
| 4,368,410 A | 1/1983 | Hance et al. | |
| 4,385,413 A | 5/1983 | Goldsmith | |
| 4,393,734 A | 7/1983 | Thorn et al. | |
| 4,395,392 A | 7/1983 | Wolgemuth | |
| 4,399,003 A | 8/1983 | Sarig et al. | |
| 4,414,045 A | 11/1983 | Wang et al. | |
| 4,425,115 A | 1/1984 | Wuchinich | |
| 4,428,748 A | 1/1984 | Peyman et al. | |
| 4,445,509 A | 5/1984 | Auth | |
| 4,447,455 A | 5/1984 | Madaus et al. | |
| 4,462,242 A | 7/1984 | Morgenthaler | |
| 4,467,678 A | 8/1984 | Lindholm | |
| 4,474,180 A | 10/1984 | Angulo | 128/328 |
| 4,479,585 A | 10/1984 | Sandhaus | |
| 4,480,642 A | 11/1984 | Stoy et al. | |
| 4,483,571 A | 11/1984 | Mishiro | |
| 4,486,680 A | 12/1984 | Bonnet et al. | 310/323.19 |
| 4,493,694 A | 1/1985 | Wuchinich | 604/22 |
| 4,498,025 A | 2/1985 | Takahashi | |
| 4,504,264 A | 3/1985 | Kelman | 604/22 |
| 4,516,398 A | 5/1985 | Wuchinich | |
| 4,523,122 A | 6/1985 | Tone et al. | |
| 4,526,571 A | 7/1985 | Wuchinich | 604/22 |
| 4,529,115 A | 7/1985 | Renshaw et al. | |
| 4,530,138 A | 7/1985 | Ritter | |
| 4,534,819 A | 8/1985 | Payet et al. | |
| 4,535,659 A | 8/1985 | Yang | |
| 4,535,759 A | 8/1985 | Polk et al. | 128/24 A |
| 4,571,520 A | 2/1986 | Saito et al. | |
| 4,572,041 A | 2/1986 | Rissmann | |
| 4,576,177 A | 3/1986 | Webster, Jr. | |
| 4,583,365 A | 4/1986 | John | |
| 4,587,958 A | 5/1986 | Noguchi et al. | |
| 4,589,415 A | 5/1986 | Haaga | |
| 4,601,705 A | 7/1986 | McCoy | |
| 4,603,694 A | 8/1986 | Wheeler | |
| 4,605,454 A | 8/1986 | Sayovitz et al. | |
| 4,607,185 A | 8/1986 | Elbert et al. | |
| 4,609,368 A | 9/1986 | Dotson, Jr. | |
| 4,620,545 A | 11/1986 | Shene et al. | |
| 4,633,119 A | 12/1986 | Thompson | |
| 4,634,420 A | 1/1987 | Spinosa et al. | 604/22 |
| 4,642,509 A | 2/1987 | Kumada | |
| 4,643,717 A | 2/1987 | Cook et al. | |
| 4,647,336 A | 3/1987 | Coenen et al. | |
| 4,647,871 A | 3/1987 | Turner, Jr. | |
| 4,651,043 A | 3/1987 | Harris et al. | |
| 4,652,785 A | 3/1987 | Gabriel et al. | |
| 4,652,786 A | 3/1987 | Mishiro | |
| 4,655,104 A | 4/1987 | Blattner | |
| 4,663,556 A | 5/1987 | Kumada | |
| 4,676,975 A | 6/1987 | McGary et al. | |
| 4,678,993 A | 7/1987 | Vinnemann et al. | |
| 4,688,454 A | 8/1987 | Scull | |
| 4,690,722 A | 9/1987 | Flood | |
| 4,692,139 A | 9/1987 | Stiles | |

| | | | | | |
|---|---|---|---|---|---|
| 4,696,299 A | 9/1987 | Shene et al. | 4,966,148 A | 10/1990 | Millar |
| 4,702,236 A | 10/1987 | Tarabichy et al. | 4,974,581 A | 12/1990 | Wiksell |
| 4,704,131 A | 11/1987 | Noishiki et al. | 4,978,333 A | 12/1990 | Broadwin et al. |
| 4,704,573 A | 11/1987 | Turner, Jr. | 4,979,952 A | 12/1990 | Kubota et al. |
| 4,708,127 A | 11/1987 | Abdelghani | 4,986,808 A | 1/1991 | Broadwin et al. |
| 4,713,132 A | 12/1987 | Abel et al. | 4,989,583 A | 2/1991 | Hood ................. 128/24 A |
| 4,715,078 A | 12/1987 | Howard et al. | 4,989,588 A | 2/1991 | Kubota et al. |
| 4,718,907 A | 1/1988 | Karwoski et al. | 5,003,965 A | 4/1991 | Talish et al. |
| 4,730,614 A | 3/1988 | Lacruche et al. | 5,003,990 A | 4/1991 | Osypka |
| 4,732,152 A | 3/1988 | Wallsten et al. | 5,015,221 A | 5/1991 | Smith |
| 4,732,156 A | 3/1988 | Nakamura | 5,015,227 A | 5/1991 | Broadwin et al. ............ 604/22 |
| 4,735,625 A | 4/1988 | Davidson | 5,017,379 A | 5/1991 | Lemelson |
| 4,738,666 A | 4/1988 | Fuqua | 5,019,083 A | 5/1991 | Klapper et al. |
| 4,738,667 A | 4/1988 | Galloway | 5,024,234 A | 6/1991 | Leary et al. |
| 4,747,820 A | 5/1988 | Hornlein et al. | 5,026,387 A | 6/1991 | Thomas ................... 606/169 |
| 4,748,985 A | 6/1988 | Nagasaki | 5,027,792 A | 7/1991 | Meyer |
| 4,748,986 A | 6/1988 | Morrison et al. | 5,040,548 A | 8/1991 | Yock |
| 4,749,437 A | 6/1988 | Welter | 5,045,054 A | 9/1991 | Hood et al. |
| 4,750,488 A | 6/1988 | Wuchinich et al. | 5,046,497 A | 9/1991 | Millar |
| 4,750,902 A * | 6/1988 | Wuchinich et al. ........... 604/22 | 5,049,157 A | 9/1991 | Mittelmeier et al. |
| 4,751,916 A | 6/1988 | Bory | 5,054,492 A | 10/1991 | Scribner et al. |
| 4,756,304 A | 7/1988 | Watanabe | 5,055,101 A | 10/1991 | McCoy |
| 4,756,309 A | 7/1988 | Sachse et al. | 5,057,106 A | 10/1991 | Kasevich et al. |
| 4,758,222 A | 7/1988 | McCoy | 5,057,119 A | 10/1991 | Clark et al. ................. 606/169 |
| 4,758,293 A | 7/1988 | Samida | 5,057,182 A | 10/1991 | Wuchinich ............... 156/580.1 |
| 4,762,668 A | 8/1988 | Loose et al. | 5,058,570 A | 10/1991 | Idemoto et al. |
| 4,770,730 A | 9/1988 | Abe | 5,059,210 A | 10/1991 | Clark et al. ................. 606/169 |
| 4,771,202 A | 9/1988 | Takahashi | 5,061,273 A | 10/1991 | Yock |
| 4,771,782 A | 9/1988 | Millar | 5,062,827 A | 11/1991 | Wiksell ...................... 604/22 |
| 4,791,915 A | 12/1988 | Barsotti et al. | 5,064,765 A | 11/1991 | Karasikov et al. |
| 4,794,912 A | 1/1989 | Lia | 5,069,664 A | 12/1991 | Guess et al. |
| 4,823,723 A | 4/1989 | Brooks | 5,076,276 A | 12/1991 | Sakurai et al. |
| 4,823,783 A | 4/1989 | Willhite, Jr. et al. | 5,102,403 A | 4/1992 | Alt |
| 4,825,851 A | 5/1989 | Cocks et al. | 5,106,741 A | 4/1992 | Marotti et al. |
| 4,828,052 A | 5/1989 | Duran et al. | 5,108,238 A | 4/1992 | Ewing |
| 4,830,002 A | 5/1989 | Semm | 5,109,830 A | 5/1992 | Cho |
| 4,834,102 A | 5/1989 | Schwarzchild et al. | 5,112,300 A | 5/1992 | Ureche ...................... 604/22 |
| 4,838,853 A | 6/1989 | Parisi ........................ 604/22 | 5,116,343 A | 5/1992 | Ams et al. ................. 606/128 |
| 4,838,859 A | 6/1989 | Strassmann | 5,122,122 A | 6/1992 | Allgood |
| 4,844,081 A | 7/1989 | Northeved et al. | 5,123,903 A | 6/1992 | Quaid et al. |
| 4,846,161 A | 7/1989 | Roger | 5,127,405 A | 7/1992 | Alcala et al. |
| 4,846,174 A | 7/1989 | Willard et al. | 5,129,914 A | 7/1992 | Choi |
| 4,846,790 A | 7/1989 | Hornlein et al. | 5,139,496 A | 8/1992 | Hed |
| 4,850,358 A | 7/1989 | Millar | 5,139,509 A | 8/1992 | Fischer et al. |
| 4,862,573 A | 9/1989 | Kelson et al. | 5,147,316 A | 9/1992 | Castillenti |
| 4,866,491 A | 9/1989 | Solomon et al. | 5,151,085 A | 9/1992 | Sakurai et al. |
| 4,867,141 A | 9/1989 | Nakada et al. .................. 601/4 | 5,151,099 A | 9/1992 | Young et al. |
| 4,870,953 A | 10/1989 | DonMichael et al. ..... 128/24 A | 5,152,200 A | 10/1992 | Kaplan |
| 4,872,333 A | 10/1989 | Burnand | 5,152,748 A | 10/1992 | Chastagner |
| 4,873,969 A | 10/1989 | Huebsch | 5,156,143 A | 10/1992 | Bocquet et al. |
| 4,877,037 A | 10/1989 | Ko et al. | 5,163,421 A | 11/1992 | Bernstein et al. ............. 128/24 |
| 4,880,011 A | 11/1989 | Imade et al. | 5,167,619 A | 12/1992 | Wuchinich .................. 604/22 |
| 4,881,761 A | 11/1989 | Hornlein et al. | 5,169,386 A | 12/1992 | Becker et al. |
| 4,882,777 A | 11/1989 | Narula | 5,171,387 A | 12/1992 | Wuchinich .................. 156/73.3 |
| 4,885,499 A | 12/1989 | Ueha et al. | 5,175,492 A | 12/1992 | Wong et al. |
| 4,886,060 A | 12/1989 | Wiksell | 5,176,141 A | 1/1993 | Bom et al. |
| 4,886,491 A | 12/1989 | Parisi et al. ................... 304/22 | 5,176,677 A | 1/1993 | Wuchinich .................. 604/356 |
| 4,892,089 A | 1/1990 | Cocks et al. | 5,180,363 A | 1/1993 | Idemoto et al. ............... 202/32 |
| 4,904,391 A | 2/1990 | Freeman | 5,190,517 A | 3/1993 | Zieve et al. ................... 604/22 |
| 4,907,572 A | 3/1990 | Borodulin et al. | 5,193,525 A | 3/1993 | Silverstein et al. |
| 4,909,789 A | 3/1990 | Taguchi et al. | 5,195,955 A | 3/1993 | Don Michael |
| 4,917,104 A | 4/1990 | Rebell | 5,201,315 A | 4/1993 | Griffith |
| 4,920,954 A | 5/1990 | Alliger et al. ............ 128/24 A | 5,201,316 A | 4/1993 | Pomeranz et al. |
| 4,922,902 A | 5/1990 | Wuchinich et al. ............ 604/22 | 5,203,338 A | 4/1993 | Jang |
| 4,924,863 A | 5/1990 | Sterzer | 5,209,719 A | 5/1993 | Baruch et al. |
| 4,931,047 A | 6/1990 | Broadwin et al. ............ 604/22 | 5,217,465 A | 6/1993 | Steppe |
| 4,931,049 A | 6/1990 | Klimas | 5,221,282 A | 6/1993 | Wuchinich .................. 606/99 |
| 4,936,281 A | 6/1990 | Stasz | 5,222,937 A | 6/1993 | Kagawa |
| 4,960,410 A | 10/1990 | Pinchuk | 5,222,974 A | 6/1993 | Kensey et al. |
| 4,961,424 A | 10/1990 | Kubota et al. ............ 128/24 A | 5,231,080 A | 7/1993 | Scholkens |
| 4,962,755 A | 10/1990 | King et al. .................... 601/2 | 5,231,994 A | 8/1993 | Harmjanz |
| 4,963,151 A | 10/1990 | Ducheyne et al. | 5,232,451 A | 8/1993 | Freitas et al. |
| 4,966,131 A | 10/1990 | Houghton et al. | 5,235,964 A | 8/1993 | Abenaim |

| | | | | | | |
|---|---|---|---|---|---|---|
| 5,240,437 A | 8/1993 | Christian | | 5,396,902 A | 3/1995 | Brennen et al. |
| 5,243,997 A | 9/1993 | Uflacker et al. ............ 600/565 | | 5,397,293 A | 3/1995 | Alliger et al. ................. 601/2 |
| 5,248,296 A | 9/1993 | Alliger | | 5,397,301 A | 3/1995 | Pflueger et al. ............... 604/22 |
| 5,249,580 A | 10/1993 | Griffith | | 5,402,799 A | 4/1995 | Colon et al. |
| 5,255,551 A | 10/1993 | Vetter | | 5,403,324 A | 4/1995 | Ciervo et al. |
| 5,255,669 A | 10/1993 | Kubota et al. | | 5,405,318 A | 4/1995 | Nita ............................ 604/22 |
| 5,261,805 A | 11/1993 | Gates | | 5,405,341 A | 4/1995 | Martin |
| 5,261,877 A | 11/1993 | Fine et al. | | 5,406,503 A | 4/1995 | Williams, Jr. et al. |
| 5,263,928 A | 11/1993 | Trauthen et al. | | 5,409,112 A | 4/1995 | Sagstetter |
| 5,263,932 A | 11/1993 | Jang | | 5,417,654 A | 5/1995 | Kelman ....................... 604/22 |
| 5,267,954 A | 12/1993 | Nita ............................ 604/22 | | 5,417,672 A | 5/1995 | Nita et al. ................... 604/533 |
| 5,267,958 A | 12/1993 | Buchbinder et al. | | 5,419,761 A | 5/1995 | Narayanan et al. |
| 5,267,982 A | 12/1993 | Sylvanowicz | | 5,421,338 A | 6/1995 | Crowley et al. |
| 5,269,297 A | 12/1993 | Weng et al. ............. 128/24 AA | | 5,421,829 A | 6/1995 | Olichney et al. |
| 5,271,735 A | 12/1993 | Greenfield et al. .......... 604/266 | | 5,423,797 A | 6/1995 | Adrian et al. |
| 5,274,297 A | 12/1993 | Hermann et al. | | 5,423,838 A | 6/1995 | Willard |
| 5,285,795 A | 2/1994 | Ryan et al. | | 5,425,704 A | 6/1995 | Sakurai et al. |
| 5,287,775 A | 2/1994 | Moore | | 5,427,118 A | 6/1995 | Nita et al. ................... 128/772 |
| 5,290,229 A | 3/1994 | Paskar | | 5,429,136 A | 7/1995 | Milo et al. |
| 5,300,021 A | 4/1994 | Wuchinich ................... 604/22 | | 5,431,664 A | 7/1995 | Ureche et al. |
| 5,300,032 A | 4/1994 | Hibbs et al. | | 5,434,827 A | 7/1995 | Bolorforosh |
| 5,300,085 A | 4/1994 | Yock | | 5,443,443 A | 8/1995 | Shiber |
| 5,304,115 A | 4/1994 | Pflueger et al. ............... 604/22 | | 5,443,456 A | 8/1995 | Alliger et al. |
| 5,304,131 A | 4/1994 | Paskar | | 5,443,457 A | 8/1995 | Ginn et al. |
| 5,304,199 A | 4/1994 | Myers | | 5,443,468 A | 8/1995 | Johnson |
| 5,306,261 A | 4/1994 | Alliger et al. | | 5,445,617 A | 8/1995 | Yoon |
| 5,307,816 A | 5/1994 | Hashimoto et al. | | 5,447,509 A | 9/1995 | Mills et al. ..................... 606/1 |
| 5,311,858 A | 5/1994 | Adair | | 5,449,369 A | 9/1995 | Imran |
| 5,312,328 A | 5/1994 | Nita et al. ..................... 604/22 | | 5,451,233 A | 9/1995 | Yock |
| 5,312,329 A | 5/1994 | Beaty et al. .................... 604/22 | | 5,452,611 A | 9/1995 | Jones et al. |
| 5,312,427 A | 5/1994 | Shturman | | 5,454,373 A | 10/1995 | Koger et al. |
| 5,315,996 A | 5/1994 | Lundquist | | 5,458,584 A | 10/1995 | Ginn et al. |
| 5,318,528 A | 6/1994 | Heaven et al. | | 5,458,612 A | 10/1995 | Chin .......................... 606/192 |
| 5,319,278 A | 6/1994 | Myohga et al. | | 5,460,595 A | 10/1995 | Hall et al. |
| 5,323,902 A | 6/1994 | Palmer et al. | | 5,462,530 A | 10/1995 | Jang |
| 5,324,255 A | 6/1994 | Passafaro et al. | | 5,464,016 A | 11/1995 | Nicholas et al. |
| 5,324,299 A | 6/1994 | Davison et al. ............. 606/167 | | 5,464,409 A | 11/1995 | Mohajer |
| 5,325,698 A | 7/1994 | Nagpal et al. | | 5,464,438 A | 11/1995 | Menaker |
| 5,326,342 A | 7/1994 | Pflueger et al. | | 5,467,674 A | 11/1995 | Thorn |
| 5,329,927 A | 7/1994 | Gardineer et al. | | 5,469,853 A | 11/1995 | Law et al. |
| 5,330,444 A | 7/1994 | Webler et al. | | 5,470,322 A | 11/1995 | Horzewski et al. |
| 5,330,482 A | 7/1994 | Gibbs et al. | | 5,472,441 A | 12/1995 | Edwards et al. ............... 606/41 |
| 5,330,497 A | 7/1994 | Freitas et al. | | 5,474,075 A | 12/1995 | Goldberg et al. |
| 5,331,242 A | 7/1994 | Petri | | 5,474,530 A | 12/1995 | Passafaro et al. |
| 5,334,160 A | 8/1994 | Ellis | | 5,474,531 A | 12/1995 | Carter |
| 5,334,167 A | 8/1994 | Cocanower | | 5,478,353 A | 12/1995 | Yoon |
| 5,334,183 A | 8/1994 | Wuchinich ................... 606/46 | | 5,478,558 A | 12/1995 | Eibl et al. |
| 5,336,184 A | 8/1994 | Teirstein | | 5,484,398 A | 1/1996 | Stoddard ...................... 604/22 |
| 5,336,234 A | 8/1994 | Vigil et al. | | 5,492,001 A | 2/1996 | Sasaki et al. |
| 5,336,699 A | 8/1994 | Cooke et al. | | 5,498,236 A | 3/1996 | Dubrul et al. ................. 604/22 |
| 5,342,292 A | 8/1994 | Nita et al. ..................... 604/22 | | 5,501,227 A | 3/1996 | Yock |
| 5,344,395 A | 9/1994 | Whalen et al. | | 5,505,714 A | 4/1996 | Dassa et al. |
| 5,350,395 A | 9/1994 | Yock | | 5,507,738 A | 4/1996 | Ciervo |
| 5,351,679 A | 10/1994 | Mayzels et al. | | 5,512,037 A | 4/1996 | Russell et al. |
| 5,353,798 A | 10/1994 | Sieben | | 5,516,043 A | 5/1996 | Manna et al. ............. 239/102.2 |
| 5,356,385 A | 10/1994 | Latini | | 5,524,620 A | 6/1996 | Rosenschein |
| 5,356,421 A | 10/1994 | Castro | | 5,524,635 A | 6/1996 | Uflacker et al. |
| 5,358,505 A | 10/1994 | Wuchinich ................... 606/99 | | 5,527,273 A | 6/1996 | Manna et al. |
| 5,362,309 A | 11/1994 | Carter | | 5,527,279 A | 6/1996 | Imran |
| 5,366,490 A | 11/1994 | Edwards et al. ............... 607/99 | | 5,531,664 A | 7/1996 | Adachi et al. |
| 5,366,899 A | 11/1994 | Shabalin et al. | | 5,536,250 A | 7/1996 | Klein et al. |
| 5,368,557 A | 11/1994 | Nita et al. | | 5,540,656 A | 7/1996 | Pflueger et al. |
| 5,368,558 A | 11/1994 | Nita ............................ 604/22 | | 5,542,917 A | 8/1996 | Nita et al. |
| 5,370,602 A | 12/1994 | Kepley | | 5,549,563 A | 8/1996 | Kronner |
| 5,380,273 A * | 1/1995 | Dubrul et al. ................. 604/22 | | 5,549,576 A | 8/1996 | Patterson et al. |
| 5,380,274 A | 1/1995 | Nita ............................ 604/22 | | 5,562,620 A | 10/1996 | Klein et al. |
| 5,382,228 A | 1/1995 | Nita et al. ..................... 604/22 | | 5,569,276 A | 10/1996 | Jang et al. |
| 5,385,372 A | 1/1995 | Utterberg | | 5,571,014 A | 11/1996 | Gregory, Jr. et al. |
| 5,387,190 A | 2/1995 | Gotanda et al. | | 5,571,085 A | 11/1996 | Accisano, III |
| 5,387,197 A | 2/1995 | Smith et al. | | 5,575,772 A | 11/1996 | Lennox |
| 5,388,569 A | 2/1995 | Kepley | | 5,580,962 A | 12/1996 | Eibl et al. |
| 5,390,678 A | 2/1995 | Gesswein et al. | | 5,582,588 A | 12/1996 | Sakurai et al. |
| 5,391,144 A | 2/1995 | Sakurai et al. | | 5,588,432 A | 12/1996 | Crowley |

| | | | | | | |
|---|---|---|---|---|---|---|
| 5,590,653 A | 1/1997 | Aida et al. | | 5,868,778 A | 2/1999 | Gershony et al. |
| 5,593,394 A | 1/1997 | Kanesaka et al. | | 5,875,782 A | 3/1999 | Ferrari et al. |
| 5,599,326 A | 2/1997 | Carter | | 5,882,347 A | 3/1999 | Mouris-Laan et al. |
| 5,603,445 A | 2/1997 | Hill et al. ............... 228/4.5 | | 5,890,406 A | 4/1999 | Thorn |
| 5,607,404 A | 3/1997 | Khairkhahan | | 5,891,149 A | 4/1999 | Young et al. ............ 606/80 |
| 5,607,440 A | 3/1997 | Danks et al. | | 5,895,370 A | 4/1999 | Edwards et al. .......... 604/22 |
| 5,611,807 A | 3/1997 | O'Boyle | | 5,895,997 A | 4/1999 | Puskas et al. |
| 5,622,170 A | 4/1997 | Schulz | | 5,897,557 A | 4/1999 | Chin et al. |
| 5,628,743 A | 5/1997 | Cimino ..................... 606/1 | | 5,897,569 A | 4/1999 | Kellogg et al. |
| 5,630,427 A | 5/1997 | Hastings | | 5,902,289 A | 5/1999 | Swartz et al. |
| 5,630,797 A | 5/1997 | Diedrich et al. | | 5,904,670 A | 5/1999 | Schreiner |
| 5,630,837 A | 5/1997 | Crowley ..................... 601/2 | | 5,906,628 A | 5/1999 | Miyawaki et al. |
| 5,647,846 A | 7/1997 | Berg et al. | | 5,908,381 A | 6/1999 | Aznoian et al. |
| 5,651,364 A | 7/1997 | Yock | | 5,910,129 A | 6/1999 | Koblish et al. |
| 5,651,776 A | 7/1997 | Appling et al. | | 5,916,192 A | 6/1999 | Nita et al. |
| 5,662,620 A | 9/1997 | Lieber et al. | | 5,916,210 A | 6/1999 | Winston |
| 5,666,970 A | 9/1997 | Smith | | 5,919,163 A | 7/1999 | Glickman |
| 5,669,881 A | 9/1997 | Dunshee | | 5,919,174 A | 7/1999 | Hanson |
| 5,672,172 A | 9/1997 | Zupkas ..................... 606/20 | | 5,920,395 A | 7/1999 | Schulz |
| 5,676,011 A | 10/1997 | Allison | | 5,921,915 A | 7/1999 | Aznoian et al. |
| 5,676,649 A | 10/1997 | Boukhny et al. | | 5,925,016 A | 7/1999 | Chornenky et al. |
| 5,681,296 A | 10/1997 | Ishida | | 5,928,218 A | 7/1999 | Gelbfish |
| 5,685,312 A | 11/1997 | Yock | | 5,931,805 A | 8/1999 | Brisken .................... 604/22 |
| 5,687,474 A | 11/1997 | Hamzehdoost et al. | | 5,935,096 A | 8/1999 | Barrett ..................... 604/22 |
| 5,688,235 A | 11/1997 | Sakurai et al. | | 5,935,142 A | 8/1999 | Hood ..................... 606/169 |
| 5,690,611 A | 11/1997 | Swartz et al. | | 5,935,143 A | 8/1999 | Hood |
| 5,693,029 A | 12/1997 | Leonhardt | | 5,944,687 A | 8/1999 | Benett et al. |
| 5,704,787 A | 1/1998 | Hickok et al. | | 5,951,480 A | 9/1999 | White et al. |
| 5,707,359 A | 1/1998 | Bufalini | | 5,951,539 A | 9/1999 | Nita et al. |
| 5,709,120 A | 1/1998 | Shilling | | 5,951,583 A | 9/1999 | Jensen et al. |
| 5,713,363 A | 2/1998 | Seward et al. | | 5,957,882 A | 9/1999 | Nita et al. ............... 604/22 |
| 5,713,848 A | 2/1998 | Dubrul et al. .............. 604/22 | | 5,961,444 A | 10/1999 | Thompson |
| 5,715,825 A | 2/1998 | Crowley | | 5,964,756 A | 10/1999 | McGaffigan et al. .......... 606/41 |
| 5,720,300 A | 2/1998 | Fagan et al. | | 5,971,949 A * | 10/1999 | Levin et al. ............. 606/169 |
| 5,720,710 A | 2/1998 | Tachibana et al. ........... 601/2 | | 5,971,960 A | 10/1999 | Flom et al. |
| 5,722,627 A | 3/1998 | Hoshino | | 5,971,983 A | 10/1999 | Lesh |
| 5,725,494 A | 3/1998 | Brisken .................... 604/22 | | 5,974,884 A | 11/1999 | Sano et al. |
| 5,728,062 A | 3/1998 | Brisken .................... 604/22 | | 5,976,093 A | 11/1999 | Jang |
| 5,735,811 A | 4/1998 | Brisken .................... 604/22 | | 5,980,563 A | 11/1999 | Tu et al. |
| 5,741,225 A | 4/1998 | Lax et al. .................. 604/22 | | 5,981,444 A | 11/1999 | Sawada et al. |
| 5,749,889 A | 5/1998 | Bacich et al. | | 5,984,882 A | 11/1999 | Rosenschein et al. |
| 5,749,914 A | 5/1998 | Janssen | | 5,984,950 A | 11/1999 | Cragg et al. |
| 5,752,932 A | 5/1998 | Ellis et al. | | 5,987,349 A | 11/1999 | Schulz |
| 5,758,420 A | 6/1998 | Schmidt et al. | | 5,989,208 A | 11/1999 | Nita ........................ 604/22 |
| 5,765,418 A | 6/1998 | Rosenberg | | 5,989,209 A | 11/1999 | Barrett ..................... 604/22 |
| 5,769,868 A | 6/1998 | Yock | | 5,989,274 A | 11/1999 | Davison et al. ............. 606/169 |
| 5,772,627 A | 6/1998 | Acosta et al. ............... 604/22 | | 5,993,408 A | 11/1999 | Zaleski |
| 5,775,328 A | 7/1998 | Lowe et al. | | 5,997,497 A | 12/1999 | Nita et al. |
| 5,776,065 A | 7/1998 | Mehmanpazir et al. | | 5,997,523 A | 12/1999 | Jang |
| 5,782,861 A | 7/1998 | Cragg et al. | | 6,001,355 A | 12/1999 | Dowdle |
| 5,797,920 A | 8/1998 | Kim | | 6,004,269 A | 12/1999 | Crowley et al. |
| 5,803,083 A | 9/1998 | Buck et al. | | 6,007,514 A | 12/1999 | Nita |
| 5,810,860 A | 9/1998 | Adrian | | 6,010,476 A | 1/2000 | Saadat |
| 5,813,998 A | 9/1998 | Dias | | 6,010,498 A | 1/2000 | Guglielmi |
| 5,824,042 A | 10/1998 | Lombardi et al. | | 6,017,340 A | 1/2000 | Cassidy et al. |
| 5,827,203 A | 10/1998 | Nita ........................... 601/2 | | 6,017,354 A | 1/2000 | Culp et al. |
| 5,827,229 A | 10/1998 | Auth et al. | | 6,017,359 A | 1/2000 | Gershony et al. |
| 5,830,125 A | 11/1998 | Scribner et al. | | 6,019,777 A | 2/2000 | Mackenzie |
| 5,830,127 A * | 11/1998 | DeCastro ................... 600/157 | | 6,021,694 A | 2/2000 | Beger |
| 5,830,195 A | 11/1998 | Peters et al. | | 6,022,336 A | 2/2000 | Zadno-Azizi et al. |
| 5,833,644 A | 11/1998 | Zadno-Azizi et al. | | 6,022,369 A | 2/2000 | Jacobsen et al. |
| 5,833,650 A | 11/1998 | Imran | | 6,027,515 A | 2/2000 | Cimino |
| 5,836,306 A | 11/1998 | Duane et al. | | 6,032,078 A | 2/2000 | Rudie ..................... 607/101 |
| 5,836,896 A | 11/1998 | Rosenschein ............... 601/2 | | 6,033,375 A | 3/2000 | Brumbach |
| 5,836,897 A | 11/1998 | Sakuri et al. ................ 601/2 | | 6,033,411 A | 3/2000 | Preissman |
| 5,840,027 A | 11/1998 | Swartz et al. | | 6,036,671 A | 3/2000 | Frey |
| 5,840,031 A | 11/1998 | Crowley | | 6,036,697 A | 3/2000 | DiCaprio |
| 5,840,151 A | 11/1998 | Munsch | | 6,036,715 A | 3/2000 | Yock |
| 5,843,017 A | 12/1998 | Yoon ........................ 604/22 | | 6,039,693 A | 3/2000 | Seward et al. |
| 5,846,218 A | 12/1998 | Brisken et al. .............. 604/22 | | 6,039,762 A | 3/2000 | McKay |
| 5,849,009 A | 12/1998 | Bernaz | | 6,045,527 A | 4/2000 | Appelbaum et al. |
| 5,861,023 A | 1/1999 | Vachon | | 6,048,329 A | 4/2000 | Thompson et al. |
| 5,868,773 A | 2/1999 | Danks et al. | | 6,050,949 A | 4/2000 | White et al. |

| | | | |
|---|---|---|---|
| 6,051,772 A | 4/2000 | Cameron et al. | |
| 6,053,904 A | 4/2000 | Scribner et al. | |
| RE36,693 E | 5/2000 | Reich | |
| 6,056,722 A | 5/2000 | Jayaraman | |
| 6,057,798 A | 5/2000 | Burrier et al. | |
| 6,059,789 A | 5/2000 | Dinger et al. | |
| 6,062,001 A | 5/2000 | Kunik | |
| 6,062,059 A | 5/2000 | Feldcamp | |
| 6,068,610 A | 5/2000 | Ellis et al. | |
| 6,077,285 A | 6/2000 | Boukhny | 606/169 |
| 6,083,191 A | 7/2000 | Rose | |
| 6,083,501 A | 7/2000 | Miyata et al. | |
| 6,090,118 A | 7/2000 | McGuckin, Jr. | |
| 6,099,464 A | 8/2000 | Shimizu et al. | |
| 6,106,475 A | 8/2000 | Lowe et al. | |
| 6,106,538 A | 8/2000 | Shiber | |
| 6,107,161 A | 8/2000 | Kitaguro et al. | |
| 6,110,142 A | 8/2000 | Pinchuk et al. | |
| 6,110,176 A | 8/2000 | Shapira | |
| 6,113,558 A | 9/2000 | Rosenschein et al. | |
| 6,113,570 A | 9/2000 | Siegel et al. | |
| 6,113,580 A | 9/2000 | Dolisi | |
| 6,123,718 A | 9/2000 | Tu et al. | |
| 6,124,150 A | 9/2000 | Corisis | |
| 6,124,546 A | 9/2000 | Hayward et al. | |
| 6,124,634 A | 9/2000 | Akram et al. | |
| 6,129,672 A | 10/2000 | Seward et al. | |
| 6,146,380 A | 11/2000 | Racz et al. | |
| 6,146,381 A | 11/2000 | Bowe et al. | |
| 6,156,018 A | 12/2000 | Hassett | |
| 6,159,195 A | 12/2000 | Ha et al. | |
| 6,162,053 A | 12/2000 | Hollander | |
| 6,165,197 A | 12/2000 | Yock | |
| 6,190,353 B1 | 2/2001 | Makower et al. | |
| 6,193,683 B1 | 2/2001 | Ludin et al. | |
| 6,200,269 B1 | 3/2001 | Lin et al. | |
| 6,200,315 B1 | 3/2001 | Gaiser et al. | |
| 6,203,516 B1 | 3/2001 | Kepley | |
| 6,203,568 B1 | 3/2001 | Lombardi et al. | |
| 6,224,565 B1 | 5/2001 | Cimino | |
| 6,228,046 B1 | 5/2001 | Brisken | |
| 6,231,514 B1 | 5/2001 | Lowe et al. | |
| 6,231,518 B1 | 5/2001 | Grabek et al. | |
| 6,234,971 B1 | 5/2001 | Jang | |
| 6,235,000 B1 | 5/2001 | Milo et al. | |
| 6,241,703 B1 | 6/2001 | Levin et al. | |
| 6,245,095 B1 | 6/2001 | Dobak, III et al. | |
| 6,247,592 B1 | 6/2001 | Racicot et al. | |
| 6,254,622 B1 * | 7/2001 | Hood | 606/169 |
| 6,258,798 B1 | 7/2001 | Wallentin | |
| 6,262,062 B1 | 7/2001 | Clemens | |
| 6,270,460 B1 | 8/2001 | McCartan et al. | |
| 6,277,084 B1 | 8/2001 | Abele et al. | |
| 6,279,743 B1 | 8/2001 | Ballard et al. | |
| 6,280,413 B1 | 8/2001 | Clark et al. | |
| 6,283,951 B1 | 9/2001 | Flaherty et al. | |
| 6,287,271 B1 | 9/2001 | Dubrul et al. | |
| 6,287,272 B1 | 9/2001 | Brisken et al. | |
| 6,290,662 B1 | 9/2001 | Morris et al. | |
| 6,290,673 B1 | 9/2001 | Shanley | |
| 6,293,725 B1 | 9/2001 | Winkvist | |
| 6,296,658 B1 | 10/2001 | Gershony et al. | |
| 6,303,635 B1 | 10/2001 | Kawai et al. | |
| 6,306,097 B1 | 10/2001 | Park et al. | |
| 6,307,156 B1 | 10/2001 | Avellanet | |
| 6,309,379 B1 | 10/2001 | Willard et al. | |
| 6,312,406 B1 | 11/2001 | Jayaraman | |
| 6,322,541 B2 | 11/2001 | West et al. | |
| 6,329,778 B1 | 12/2001 | Culp et al. | |
| 6,346,091 B1 | 2/2002 | Jacobsen et al. | |
| 6,348,039 B1 | 2/2002 | Flachman et al. | |
| 6,358,252 B1 | 3/2002 | Shapira | |
| 6,364,840 B1 | 4/2002 | Crowley | |
| 6,364,841 B1 | 4/2002 | White et al. | |
| 6,368,611 B1 | 4/2002 | Whitbourne et al. | |
| 6,376,513 B1 | 4/2002 | Akahane et al. | |
| 6,383,151 B1 | 5/2002 | Diederich et al. | |
| 6,387,109 B1 * | 5/2002 | Davison et al. | 606/169 |
| 6,391,042 B1 | 5/2002 | Cimino | |
| 6,396,293 B1 | 5/2002 | Vinther et al. | |
| 6,398,776 B1 | 6/2002 | Sekino et al. | |
| 6,398,792 B1 | 6/2002 | O'Connor | |
| 6,410,560 B1 | 6/2002 | Akahane et al. | |
| 6,416,511 B1 | 7/2002 | Lesh et al. | |
| 6,416,530 B2 | 7/2002 | DeVries et al. | |
| 6,416,737 B1 | 7/2002 | Manolagas et al. | |
| 6,419,644 B1 | 7/2002 | White et al. | |
| 6,433,464 B2 | 8/2002 | Jones | |
| 6,440,726 B1 | 8/2002 | Resnick | |
| 6,440,947 B1 | 8/2002 | Barron et al. | |
| 6,443,903 B1 | 9/2002 | White et al. | |
| 6,450,975 B1 | 9/2002 | Brennan et al. | |
| 6,451,303 B1 | 9/2002 | Whitehouse et al. | |
| 6,454,737 B1 | 9/2002 | Nita et al. | |
| 6,454,757 B1 | 9/2002 | Nita et al. | |
| 6,457,365 B1 | 10/2002 | Stephens et al. | |
| 6,458,375 B1 | 10/2002 | Gertzman et al. | |
| 6,462,172 B1 | 10/2002 | Maclennan et al. | |
| 6,464,660 B2 | 10/2002 | Brisken et al. | |
| 6,469,419 B2 | 10/2002 | Kato et al. | |
| 6,471,656 B1 | 10/2002 | Shalman et al. | |
| 6,475,185 B1 | 11/2002 | Rauker et al. | |
| 6,478,751 B1 | 11/2002 | Krueger et al. | |
| 6,482,218 B1 | 11/2002 | Tran | |
| 6,485,481 B1 | 11/2002 | Pfeiffer | |
| 6,491,710 B2 | 12/2002 | Satake | |
| 6,491,711 B1 | 12/2002 | Durcan | |
| 6,494,883 B1 | 12/2002 | Ferree | |
| 6,494,885 B1 | 12/2002 | Dhindsa | |
| 6,494,891 B1 | 12/2002 | Cornish et al. | |
| 6,494,893 B2 | 12/2002 | Dubrul et al. | |
| 6,497,667 B1 | 12/2002 | Miller et al. | |
| 6,497,698 B1 | 12/2002 | Fonger et al. | |
| 6,503,223 B1 | 1/2003 | Sekido et al. | |
| 6,508,781 B1 | 1/2003 | Brennan et al. | |
| 6,508,782 B1 | 1/2003 | Evans et al. | |
| 6,509,348 B1 | 1/2003 | Ogletree | |
| 6,511,492 B1 | 1/2003 | Rosenbluth et al. | |
| 6,512,957 B1 | 1/2003 | Witte | |
| 6,514,210 B2 | 2/2003 | Ohara et al. | |
| 6,522,929 B2 | 2/2003 | Swing | |
| 6,524,251 B2 | 2/2003 | Rabiner et al. | |
| 6,527,115 B2 | 3/2003 | Rabiner et al. | |
| 6,530,923 B1 | 3/2003 | Dubrul et al. | |
| 6,544,276 B1 | 4/2003 | Azizi | |
| 6,544,279 B1 | 4/2003 | Hopkins et al. | |
| 6,544,541 B1 | 4/2003 | Zahradka | |
| 6,547,724 B1 | 4/2003 | Soble et al. | |
| 6,551,269 B2 | 4/2003 | Clemens et al. | |
| 6,551,327 B1 | 4/2003 | Dhindsa | |
| 6,551,337 B1 * | 4/2003 | Rabiner et al. | 606/169 |
| 6,558,334 B2 | 5/2003 | Shalman et al. | |
| 6,569,109 B2 | 5/2003 | Sakurai et al. | |
| 6,569,148 B2 | 5/2003 | Bagaoisan et al. | |
| 6,572,555 B2 | 6/2003 | White et al. | |
| 6,575,959 B1 | 6/2003 | Sarge et al. | |
| 6,575,993 B1 | 6/2003 | Yock | |
| 6,577,042 B2 | 6/2003 | Lee et al. | |
| 6,579,277 B1 | 6/2003 | Rabiner et al. | |
| 6,579,279 B1 | 6/2003 | Rabiner et al. | |
| 6,579,302 B2 | 6/2003 | Duerig et al. | |
| 6,585,657 B2 | 7/2003 | Yock | |
| 6,589,253 B1 | 7/2003 | Cornish et al. | |
| 6,592,548 B2 | 7/2003 | Jayaraman | |
| 6,596,020 B2 | 7/2003 | Vardi et al. | |
| 6,605,074 B2 | 8/2003 | Zadno-Azizi et al. | |

| | | |
|---|---|---|
| 6,611,793 B1 | 8/2003 | Burnside et al. |
| 6,615,080 B1 | 9/2003 | Unsworth et al. |
| 6,617,760 B1 | 9/2003 | Peterson et al. |
| 6,620,113 B2 | 9/2003 | White et al. |
| 6,626,853 B2 | 9/2003 | White et al. |
| 6,626,926 B2 | 9/2003 | Friedman et al. |
| 6,629,948 B2 | 10/2003 | Rockley et al. |
| 6,645,149 B1 | 11/2003 | Smith |
| 6,645,152 B1 | 11/2003 | Jung et al. |
| 6,647,755 B2 | 11/2003 | Rabiner et al. |
| 6,648,881 B2 | 11/2003 | KenKnight et al. |
| 6,652,547 B2 | 11/2003 | Rabiner et al. |
| 6,655,386 B1 | 12/2003 | Makower et al. |
| 6,660,013 B2 | 12/2003 | Rabiner et al. |
| 6,669,665 B2 | 12/2003 | Jayaraman |
| 6,679,873 B2 | 1/2004 | Rabiner et al. |
| 6,682,556 B1 | 1/2004 | Ischinger |
| 6,689,086 B1 | 2/2004 | Nita et al. |
| 6,689,087 B2 | 2/2004 | Pal et al. |
| 6,692,460 B1 | 2/2004 | Jayaraman |
| 6,695,781 B2 | 2/2004 | Rabiner et al. |
| 6,695,782 B2 * | 2/2004 | Ranucci et al. ............. 600/439 |
| 6,702,748 B1 | 3/2004 | Nita et al. |
| 6,702,750 B2 | 3/2004 | Yock |
| 6,712,766 B2 | 3/2004 | Harada |
| 6,726,698 B2 | 4/2004 | Cimino |
| D489,973 S | 5/2004 | Root et al. |
| 6,730,037 B2 | 5/2004 | Jang |
| 6,730,048 B1 | 5/2004 | Hare et al. |
| 6,733,451 B2 | 5/2004 | Rabiner et al. |
| 6,760,165 B2 | 7/2004 | Wulff et al. |
| 6,761,690 B2 | 7/2004 | Sakurai et al. |
| 6,790,204 B2 | 9/2004 | Zadno-Azizi et al. |
| 6,802,835 B2 | 10/2004 | Rabiner et al. |
| 6,840,952 B2 | 1/2005 | Saker et al. |
| 6,849,062 B2 | 2/2005 | Kantor |
| 6,855,123 B2 | 2/2005 | Nita |
| 6,855,125 B2 | 2/2005 | Shanley |
| 6,860,876 B2 | 3/2005 | Chen |
| 6,866,670 B2 | 3/2005 | Rabiner et al. |
| 6,878,106 B1 | 4/2005 | Herrmann |
| 6,887,257 B2 | 5/2005 | Salahieh et al. |
| 6,908,472 B2 | 6/2005 | Wiener et al. |
| 6,921,411 B2 | 7/2005 | Yock |
| 6,923,788 B2 | 8/2005 | Kantor |
| 6,929,632 B2 | 8/2005 | Nita et al. |
| 6,939,317 B2 | 9/2005 | Zacharias |
| 6,942,620 B2 | 9/2005 | Nita et al. |
| 6,942,677 B2 | 9/2005 | Nita et al. |
| 6,966,891 B2 | 11/2005 | Ookubo et al. |
| 6,984,220 B2 | 1/2006 | Wuchinich |
| 2001/0047166 A1 | 11/2001 | Wuchinich |
| 2002/0007130 A1 | 1/2002 | Burbank et al. |
| 2002/0016565 A1 | 2/2002 | Zadno-Azizi et al. |
| 2002/0029014 A1 | 3/2002 | Jayaraman |
| 2002/0029054 A1 | 3/2002 | Rabiner et al. |
| 2002/0055754 A1 | 5/2002 | Ranucci et al. |
| 2002/0077550 A1 | 6/2002 | Rabiner et al. |
| 2002/0077643 A1 | 6/2002 | Rabiner et al. |
| 2002/0082503 A1 | 6/2002 | Chandrasekaran et al. |
| 2002/0091407 A1 | 7/2002 | Zadno-Azizi et al. |
| 2002/0095141 A1 | 7/2002 | Belef et al. |
| 2002/0107446 A1 | 8/2002 | Rabiner et al. |
| 2003/0009125 A1 | 1/2003 | Nita et al. |
| 2003/0045835 A1 | 3/2003 | Anderson et al. |
| 2003/0045887 A1 | 3/2003 | Sakurai et al. |
| 2003/0048037 A1 | 3/2003 | Boyd |
| 2003/0074006 A1 | 4/2003 | Mowry et al. |
| 2003/0114732 A1 | 6/2003 | Webler et al. |
| 2003/0120208 A1 | 6/2003 | Houser et al. |
| 2003/0125751 A1 | 7/2003 | Griffin et al. |
| 2003/0176791 A1 | 9/2003 | Rabiner et al. |
| 2003/0181923 A1 | 9/2003 | Vardi |
| 2003/0197958 A1 | 10/2003 | Wulff et al. |
| 2003/0212331 A1 | 11/2003 | Fenton et al. |
| 2003/0225332 A1 | 12/2003 | Okada et al. |
| 2003/0236539 A1 | 12/2003 | Rabiner et al. |
| 2004/0019266 A1 | 1/2004 | Marciante et al. |
| 2004/0024393 A1 | 2/2004 | Nita et al. |
| 2004/0024402 A1 | 2/2004 | Nita |
| 2004/0039311 A1 | 2/2004 | Nita et al. |
| 2004/0039375 A1 | 2/2004 | Miyazawa |
| 2004/0059227 A1 | 3/2004 | Nita et al. |
| 2004/0059280 A1 | 3/2004 | Makower et al. |
| 2004/0068189 A1 | 4/2004 | Wilson et al. |
| 2004/0097996 A1 | 5/2004 | Rabiner et al. |
| 2004/0106866 A1 | 6/2004 | Ookubo et al. |
| 2004/0119287 A1 | 6/2004 | Williams et al. |
| 2004/0138570 A1 | 7/2004 | Nita et al. |
| 2004/0167507 A1 | 8/2004 | Nita et al. |
| 2004/0199228 A1 | 10/2004 | Wilson |
| 2004/0204670 A1 | 10/2004 | Nita et al. |
| 2004/0204729 A1 | 10/2004 | Cimino |
| 2004/0210140 A1 | 10/2004 | Rabiner et al. |
| 2004/0213866 A1 | 10/2004 | Wulff et al. |
| 2004/0243052 A1 | 12/2004 | Kauphusman et al. |
| 2005/0043629 A1 | 2/2005 | Rabiner et al. |
| 2005/0059991 A1 | 3/2005 | Shanley |
| 2005/0070794 A1 | 3/2005 | Deal et al. |
| 2005/0101870 A1 | 5/2005 | Yamaguchi et al. |
| 2005/0101906 A1 | 5/2005 | Nita |
| 2005/0113688 A1 | 5/2005 | Nita et al. |
| 2005/0119606 A1 | 6/2005 | Nita |
| 2005/0124877 A1 | 6/2005 | Nita et al. |
| 2005/0171570 A1 | 8/2005 | Yock |
| 2005/0209677 A1 | 9/2005 | Shaked |
| 2005/0240165 A1 | 10/2005 | Miki et al. |
| 2005/0245951 A1 | 11/2005 | Nita et al. |
| 2005/0277577 A1 | 12/2005 | Hunter et al. |
| 2005/0283080 A1 | 12/2005 | Nita et al. |

FOREIGN PATENT DOCUMENTS

| | | |
|---|---|---|
| CA | 2320300 | 8/1999 |
| CA | 2 362 689 | 9/2000 |
| DE | 428980 | 5/1926 |
| DE | 203 229 | 10/1983 |
| DE | 37 31 482 | 4/1988 |
| EP | 0 121 491 | 10/1984 |
| EP | 0 243 298 | 10/1987 |
| EP | 0293472 | 12/1988 |
| EP | 0316796 A2 | 5/1989 |
| EP | 0316796 A3 | 5/1989 |
| EP | 0 353 294 | 2/1990 |
| EP | 0 493 047 | 7/1992 |
| EP | 0 542 103 | 5/1993 |
| EP | 0541249 | 5/1993 |
| EP | 0891744 | 1/1999 |
| FR | 461395 | 12/1913 |
| FR | 2 614 524 | 11/1988 |
| GB | 19559 | 9/1899 |
| GB | 1 371 335 | 10/1974 |
| GB | 2 032 221 | 4/1980 |
| GB | 2 325 192 | 11/1998 |
| JP | 63-305856 | 12/1988 |
| JP | 1-027548 | 1/1989 |
| JP | 1-288249 | 11/1989 |
| JP | 08-117240 | 5/1996 |
| WO | WO 87/01276 | 3/1987 |
| WO | WO 89/06515 | 7/1989 |
| WO | WO 90/01300 | 2/1990 |
| WO | WO 90/10423 | 9/1990 |
| WO | WO 91/07138 | 5/1991 |
| WO | WO 92/04071 | 3/1992 |
| WO | WO 92/11815 | 7/1992 |
| WO | WO 93/16646 | 9/1993 |

| | | |
|---|---|---|
| WO | WO 95/03740 | 2/1995 |
| WO | WO 96/07377 | 3/1996 |
| WO | WO 98/35721 | 8/1998 |
| WO | WO 98/40021 | 9/1998 |
| WO | WO 98/55032 | 12/1998 |
| WO | WO 99/16360 | 4/1999 |
| WO | WO 99/33404 | 7/1999 |
| WO | WO 99/35982 | 7/1999 |
| WO | WO 99/39647 | 8/1999 |
| WO | WO 00/21444 | 4/2000 |
| WO | WO 00/53263 | 9/2000 |

OTHER PUBLICATIONS

Chaussy et al., *Transurethral Ultrasonic Ureterolithotripsy Using a Solid-Wire Probe*, Urology, May 1987, vol. 29, No. 5, pp. 531-532.
Supplementary European Search Report for application No. EP00965553 dated Apr. 7, 2003.
BBI Newsletter, vol. XIII, No. 3, p. 44, Biomedical Business International, 1524 Brookhollow Drive, Santa Ana, California 92705 (1990).
Beckenbaugh, R.D. and M.S. Ilstrup, *Total Hip Arthroplasty*, J. Bone and Joint Surgery, vol. 60A, pp. 308-314 (1978).
Brochure, Endo-Urology—A Breakthrough in Ultrasonic Lithotripsy, Karl Storz Endoscopy—America, Inc. (1984).
Brochure, Instruments and Apparatus for Lithotripsy, Richard Wolf GmbH, Knittlinger, West Germany (1984).
Brochure, Percutaneous Low Pressure Universal Nephroscope, Richard Wolf, Knittlinger, West Germany (1984).
Brochure, *Sonic Surgery System*, Quintron, Inc.
Cameron, Proximal Femoral Osteotomy in Difficult Revision Hip Surgery: How to Revise the Unrevisable, 18 Contemp. Orthopaedics 565 (1989).
Caspar, Current Development of Instrumentation for Arthroscopy, *Clinics in Sports Medicine*, 6:3 (1987), pp. 626-627.
De Puy Inc., Catalog (1966).
Eisner, Physical Acoustics, 1964, pp. 353-363.
Emsinger, Ultrasonics, 1988, pp. 419-492.
Ensminger, *Ultrasonics: Fundamentals, Technology, Applications*, pp. 462-467, Marcel Dekker Inc. (1988).
Epstein et al., Surgical Management of Extensive Intramedullary Spinal Cord Astrocytoma in Children, Concepts in Pediatric Neurosurgery, 2, (1982) pp. 29-44.
Goliamina, "*Ultrasonic Surgery*", Proceedings of the Eighth Int'l. Cong. On Acoustics, London, 1974, pp. 63-69.
Gray, "Endovascular treatment of peripheral arterial disease," *Journal of the American Osteopathic Association*, 100(10):S15-S20 (Supplement to Oct. 2000).
Harris et al., A New Technique for Removal of Broken Femoral Stems in Total Hip Replacement, 63-A J. Bone & Joint Surgery 843 (1981).
Johnson, Arthroscopic Surgery: Principles and Practice (3rd Edition), Verlag Springer (1986), pp. 244-245.
Karpman et al., The Lithotriptor and Its Potential Use in the Revision of Total Hip Arthroplasty, 16 Orthopaedic Rev. 81 (1987).
Klapper and Caillouette, "*The Use of Ultrasonic Tools in Revision Arthoplasty Procedures*", 20:3 Contemporary Orthopaedics, pp. 273-279 (Mar. 1990).
Krawitt et al., Ultrasonic Aspiration of Prostate, Bladder Tumors and Stones, *Urology*, 30:6 (1987) pp. 578-580.
Lin, Posterior Lumbar Interbody Fusion Technique: Complications and Pitfalls, 193 Clinical Orthopaedics and Related Research 90 (1985).
Malloy et al., Endoscopis Ultrasonic Aspiration of the Prostate, Bladder Tumors and Stones, Journal of Urology Supplement, May 1989.
Malloy et al., Transurethral Ultrasonic Aspiration of the Prostrate, A.U.A., May 1989.
McClelland et al., Atraumatic Removal of a Well-Fixed Porous Ingrowth Hip Prosthesis, 15 Orthopaedic Rev. 75 (1986).
Moreland et al., *Techniques for Removal of Prosthesis and Cement in Total Hip Revisional Surgery*, Contemporary Orthopaedics, V. 21, No. 6, pp. 595-635, 1990.
Moreland et al., The Window Technique for the Removal of Broken Femoral Stems in Total Hip Replacement, 212 Clinical Orthopaedics and Related Research 245 (1986).
Neppiras, The Pre-Stressed Piezoelectric Sandwich Transducer, 1973, pp. 295-302.
Rayleigh, The Theory of Sound, vol. 1, 1894, pp. 255-305.
Richards Mfg. Co., Orthopedic Catalog (1981).
Richmond et al., Evaluation of the Histopathology of Brain Tumor Tisue Obtained by Ultrasonic Aspiration, *Neurosurgery*, 13:4 (1983), pp. 415-419.
Rozenberg, Sources of High-Intensity Ultrasound, vol. 2, 1973, pp. 111-114.
Sahagian, Richard, "Critical Insight: Marking Devices with Radiopaque Coatings," May 1999, *Medical Device & Diagnostic Industry Magazine* (http://www.devicelink.com/mddi/archive/99/05/011.html).
Schwartz, Jr. et al., Femoral Fracture During Non-Cemented Total Hip Arthroplasty, 71-A J. Bone & Joint Surgery 1135 (1989).
Sternlieb et al., Ultrasonic Restoration of Severely Calcified Aortic Valve, *The Lancet*, Aug. 20, 1988, p. 446.
Weis, Jr., A Sonic Tool for Spinal Fusion, 8 Orthopedic Clinics of North Am. 43 (1977).
Wick et al., "Tool and Manufacturing Engineers Handbood," Fourth Edition, vol. II, Forming, Society of Manufacturing Engineers, Dearbord, Michigan, 1983-1984, pp. 13-1 through 13-2 (spelling error?).
Zhou et al., Effect of Press-Fit Femoral Stems on Strains in the Femur, 5 J. Arthroplasty 71 (1990).

\* cited by examiner

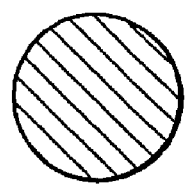
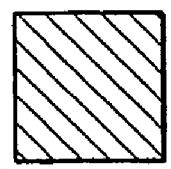
FIG. 5A        FIG. 5B
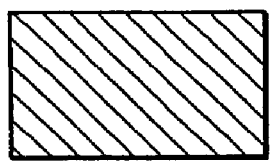
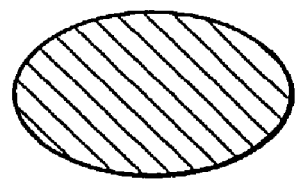
FIG. 5C        FIG. 5D
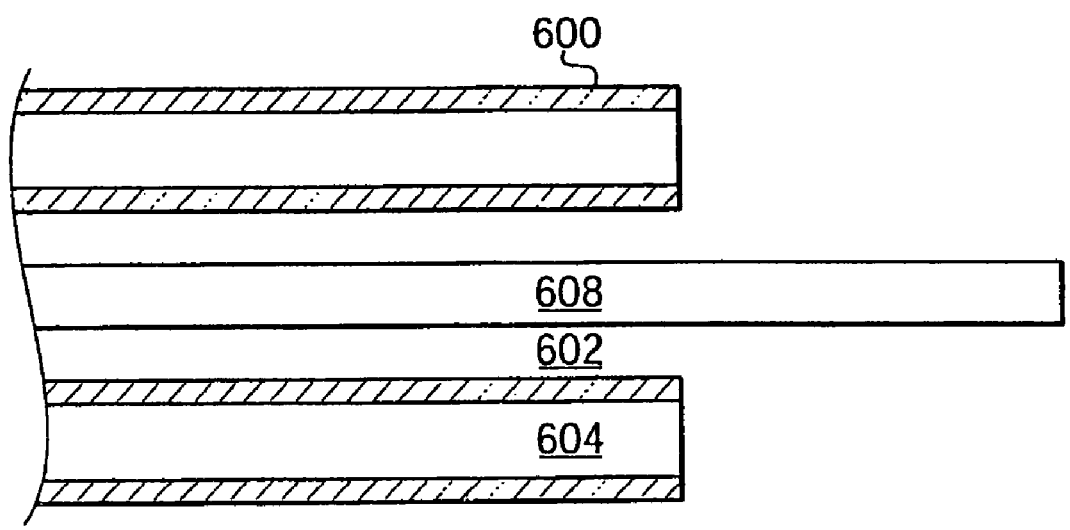
FIG. 6

ULTRASONIC MEDICAL DEVICE OPERATING IN A TRANSVERSE MODE

RELATED APPLICATIONS

This is a continuation of application Ser. No. 09/618,352, filed Jul. 19, 2000, which claims the benefit of Provisional Application Ser. No. 60/178,901, filed Jan. 28, 2000, and claims the benefit of Provisional Application Ser. No. 60/157,824, filed Oct. 5, 1999, the entirety of all these applications are hereby incorporated herein by reference.

BACKGROUND OF THE INVENTION

1. Field of the Invention

The present invention relates generally to medical devices, and more particularly to an ultrasonic medical device for destroying tissue in a controlled fashion within a human body.

2. Description of Related Art

Medical instruments utilizing ultrasonic energy to destroy tissue in a human body are known in the art. One drawback of existing ultrasonic medical instruments which remove tissue is that typically doctors have considered them to be slow in comparison to methods such as surgical excision. Part of the reason for this perceived slowness is explained by the fact that most existing ultrasonic devices rely on a longitudinal vibration of the tip of the probe. In other words, the tip of the probe is vibrated in a direction in line with the longitudinal axis of the probe. This produces a tissue destroying affect only at the tip of the probe.

One solution that has been proposed is to vibrate the tip of the probe in a transverse direction—i.e. perpendicular to the longitudinal axis of the probe—in addition to vibrating the tip in the longitudinal direction. For example, U.S. Pat. No. 4,961,424 to Kubota et al. discloses an ultrasonic treatment device to destroy and emulsify concretions or tissue in a human body. The Kubota et al. device produces both a longitudinal and transverse motion at the tip of the probe. The Kubota et al. patent, however, still relies solely on the tip of the probe to act as a working surface. Therefore, it improves the efficiency of the tip, but still relies on the tip of the probe to perform all cutting actions.

Although Kubota et al. describe providing a transverse motion at the tip of the probe, a transverse motion along the length of the probe has generally been discouraged. For example, U.S. Pat. No. 4,474,180 to Angulo discloses an ultrasonic kidney stone disintegration instrument with a damping material applied to the wire probe to inhibit lateral vibrations of the wire in the region of the connection to the ultrasonic transducer.

Another proposed method of improving the speed of ultrasonic tissue remove is oscillating the tip of the probe in addition to longitudinally vibrating the tip of the probe. For example, U.S. Pat. No. 4,504,264 to Kelman discloses an ultrasonic treatment device which improves the speed of ultrasonic tissue removal. In the Kelman device, the tip of the probe is vibrated longitudinally and also oscillated, so that the cutting efficiency of the probe tip is improved. Again, however, only the tip of the probe performs a cutting action.

BRIEF SUMMARY OF THE INVENTION

The object of the present invention is to provide an ultrasonic medical device capable of destroying and emulsifying tissue through cavitation in the human body with a higher efficiency by means of a flexible probe operating in a transverse mode. As used herein, a transverse mode of operation is used to describe a flexible probe with a plurality of nodes and anti-nodes along the length of the probe.

In accordance with this object, an ultrasonic medical device comprises an ultrasonic vibration generator that generates vibration along its longitudinal axis. The ultrasonic vibration is transmitted through an ultrasonic coupler and a series of transformer sections that amplify the ultrasonic vibration. A flexible member is coupled to the distal end of the transformer sections, and is thus supplied with a longitudinal vibration at its base by the transformer sections. The flexible member is designed so that it converts the longitudinal vibration into a standing wave that runs along the length of the flexible member. The standing wave produces a series of nodes and anti-nodes along the length of the flexible member. Each of the anti-nodes produces cavitation in fluids in contact with the probe. The cavitation of the fluids causes destruction of adjacent tissue. Thus, in this manner, the entire length of the flexible member becomes a working surface that may be utilized for destroying tissue.

Therefore, in contrast to the prior art designs that only utilize a tip of a probe as a surface, the entire length of the flexible member forms a cutting surface in the present invention.

BRIEF DESCRIPTION OF THE DRAWINGS

FIGS. 5A-5D show possible various cross-sectional profiles of a flexible member for use in the present invention; and FIG. 6 shows the ultrasonic probe and an associated sheath.

DETAILED DESCRIPTION OF THE INVENTION

Figure 1:
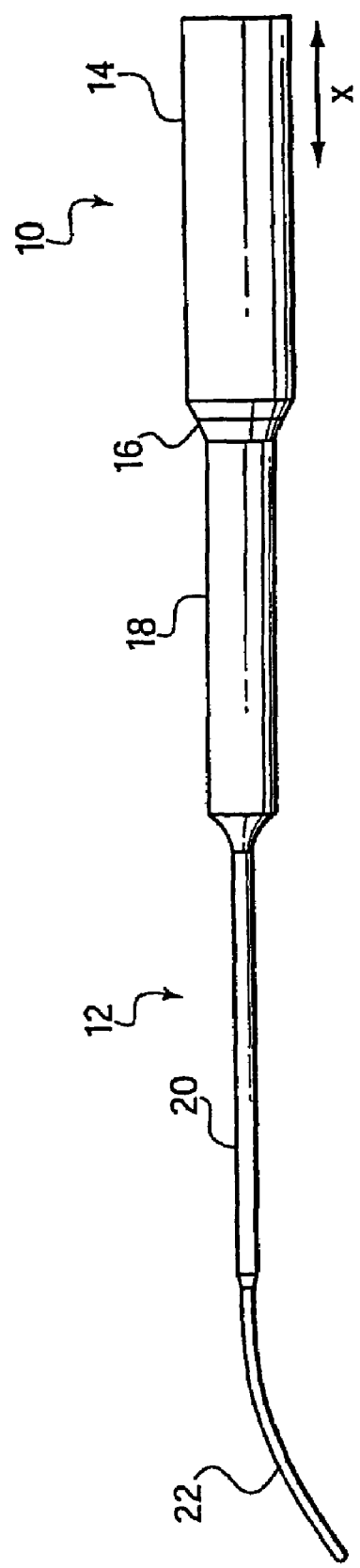
FIG. 1 shows a schematic view of an ultrasonic probe constructed in accordance with the principles of the invention.
Figure 2:
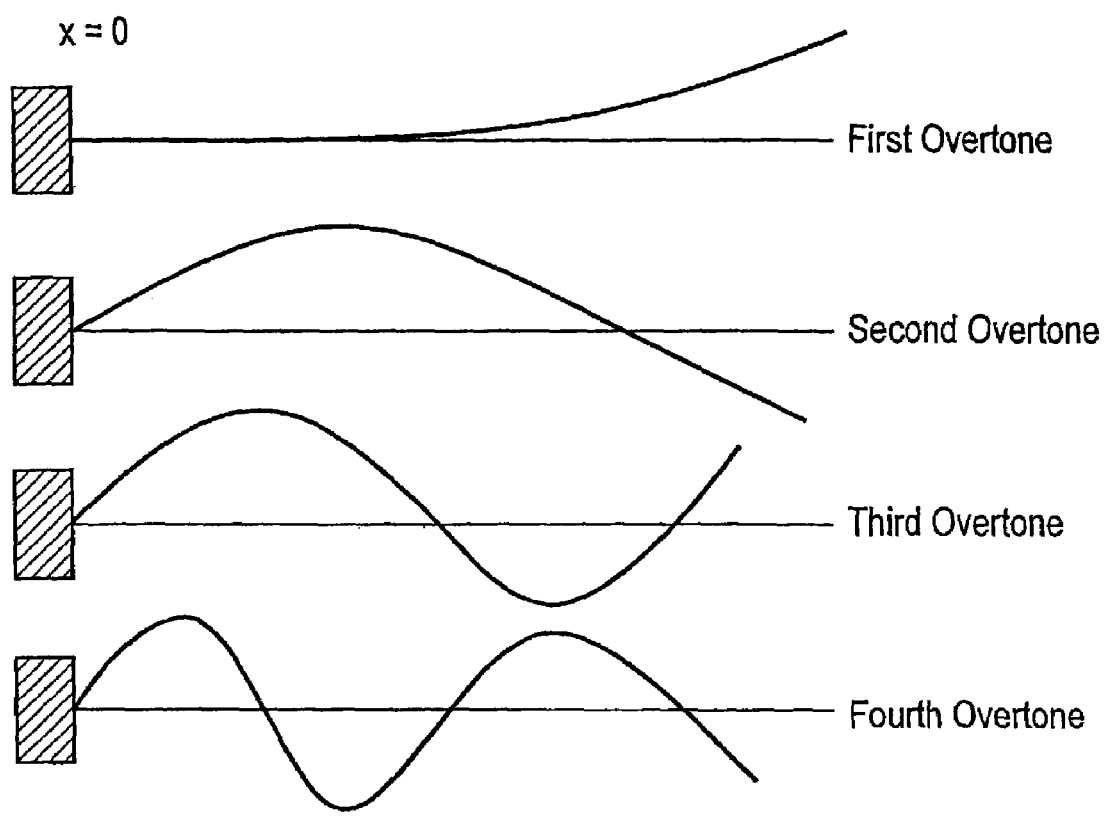
FIG. 2 shows the flexible member of the ultrasonic probe operating in a transverse mode.
Figure 3:
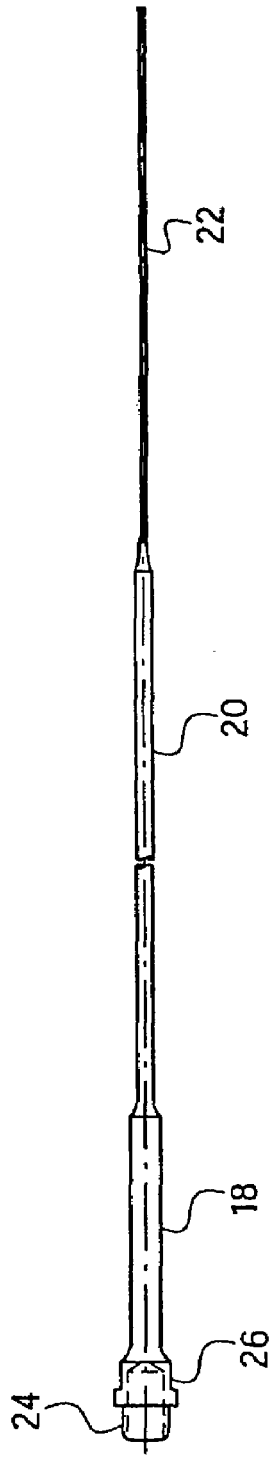
FIG. 3 shows a probe assembly for use in an ultrasonic probe constructed in accordance with the principles of the invention.

As seen in FIGS. 1 and 3, the ultrasonic probe has a handle section 10 and a probe section 12. The handle is formed by an ultrasonic driver 14 and an ultrasonic coupling horn 16. The ultrasonic driver has a longitudinal axis. The driver produces an ultrasonic vibration in the range of 20-80 kHz. The nominal driver amplitude is 50 microns at 100 volt peak to peak sinusoidal excitation. The vibration is along the direction of the longitudinal axis. In the embodiment illustrated, the transducer is PZT-4. However, the driver can utilize a variety of methods to produce an ultrasonic vibration, such as piezoelectric, magnetostrictive, pneumatic, or hydraulic, as are known to those skilled in the art. A control unit (not illustrated) controls the ultrasonic driver. The control unit allows an operator to adjust the frequency and amplitude of the vibration which is produced by the driver. In the exemplary embodiment illustrated here, the probe is designed to operate at a frequency of 20 kHz. However, the probe may be designed to operate at frequencies in the range of 20 kHz to 80 kHz, as described in detail in the theory of operation section.

The ultrasonic driver is coupled to a coupling horn 16, and the ultrasonic vibration is transmitted from the driver to the coupling horn. The coupling horn is connected to the probe section 12. The probe section has a series of transformer sections 18, 20. The transformer sections are a series of shafts constructed from any suitable material, such as Ti-6Al-4v titanium. The transformer sections transmit vibrations from the coupling horn to a flexible member 22 at the distal end of the probe section. In the process of transmission, the amplitude of the vibration is amplified by the transformer sections. The diameter of the transformer sections are chosen so as to produce a suitable amount of longitudinal vibration at the end of the transformer section. The gain of the transformer sections is controlled by the ratio of the area of the sections. In the exemplary embodiment described herein, the transformer sections are designed to produce a gain of about 4-5 over the transducer. This is achieved by setting the diameter of the transformer sections 18, 20 at 0.150 and 0.080 inches, respectively. The length of the transformer sections 18, 20 are 1.500 and 7.554 inches, respectively. The transformer section 18 has a threaded portion 24 to mate with the coupling horn 16, and has a portion 26 which is adapted so that it may be grasped with a wrench or another tool to tighten the connection.

A flexible member 22 is attached to the end of the last transformer section, and is driven by the last transformer section. The flexible member is a thin, wire like probe, typically less than 1 mm in diameter. In the embodiment shown, the flexible member has a circular cross-section with a diameter of 0.020 inches. The flexible member may have other cross-sections, such as a rectangular or oval cross-section. The flexible portion of the probe can be multiple wavelengths in length. In the embodiment shown, the flexible member is 4.046 inches long, which corresponds to a device operating with a frequency of approximately 20 kHz. The preferred material is 6Al-4v titanium; however, any other materials may be used as long as the operating parameters fall within the operation limits set by the strength of the material, as discussed in detail below.

Figure 4:
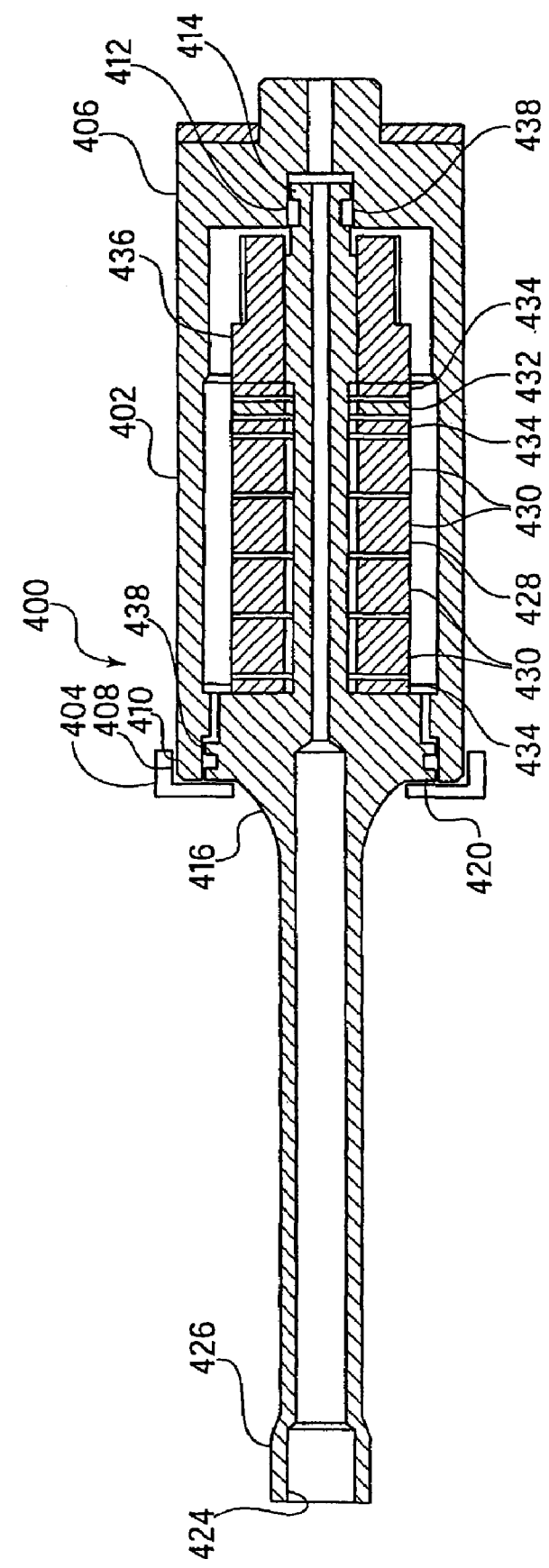
FIG. 4 shows a cross-sectional view of the handle assembly of an ultrasonic probe constructed in accordance with the principles of the invention.

FIG. 4 shows a cross-sectional view of the handle assembly of an ultrasonic probe constructed in accordance with the principles of the invention. FIG. 4 shows an exemplary horn assembly 400 suitable for use in the present invention. A housing 402 has a end cap 404 and a rear portion 406. The end cap 404 has an internal threaded portion 408 which mates with an external threaded portion 410 of the rear portion 406. The rear portion 406 of the housing 402 has a recess 412 which receives an extended portion 414 of the horn 416. The end cap 404 is shaped as a ring with a opening 418. The horn 416 fits through the opening 418. A flange 420 on the horn 416 is larger than the opening 418 so that when the end cap 404 is screwed on, the horn 416 is held tightly into the housing 402.

The horn 416 has female threads 424 at one end 426 to mate with a probe assembly. Grooves 438 are provided on the horn 416. O-rings (not shown) may be placed into the grooves to provide a substantially fluid-tight seal.

A stack of piezo-ceramic drivers 428 is arranged around the horn 416. The driver stack 428 has four driver ceramics 430, and an additional feedback ceramic 432. The feedback ceramic 432 is used to measure the driver amplitude. Each driver is provided with a nickel electrode for connection to an electrical source (not shown). The electrical source provides an alternating waveform at the appropriate frequency and amplitude. Insulators 434 are provided to isolate the piezo-ceramics from the horn and from the feedback ceramic. MACOR™ insulators, available from Corning, are one suitable type of insulator. The extended portion 414 of the horn 416 is threaded so that a nut 436 may be used to secure the piezo-ceramic drivers to the horn.

FIGS. 5A-5D show various cross-sectional profiles of ultrasonic probes which are suitable for use with the present invention. As will be discussed in detail later, any cross-sectional profile may be utilized so long as certain design constraints are met.

As seen in FIG. 6, proximal to the desired, active length 606 of the probe 608, the probe 608 is placed within a sheath 600 which can provide irrigation channels and aspiration channels 602, 604. Irrigation is preferably provided between the probe 608 and the sheath 600. The sheath 600 is preferably made of PTFE or Teflon tubing so as to absorb the ultrasonic energy emanating from portions of the probe located within the sheath, thereby allowing control over the amount of tissue affected by the probe. The sheathing is not restricted to the preferred materials as long as it is made of a material which is not heated by the ultrasonic energy, although the irrigation fluid can be used to cool the sheath material. The probe may be extended or retracted from the sheath to modify the amount of probe exposed, thereby modifying the active length 606 of the probe. Further details regarding one suitable sheath are described in Applicant's co-pending application Ser. No. 60/157,824, which is hereby incorporated by reference.

Theory of Operation of the Invention

Although, not intended to be bound by the following theory of operation, it is believed that the following theory describes the operation of the ultrasonic probe of the present invention. In operation, the longitudinal push delivered by the transformer sections causes a flexing or buckling of the thin member at the end of the probe. The buckling may be realized as a flexure or standing transverse wave along the length of the probe section. The flexure case is simply the first order transverse mode of vibration as will be described below.

In a fluid or fluid containing medium, each of the antinodes (positions corresponding to maximum transverse displacement) along the length of the probe cause cavitation of the fluid in a direction perpendicular to the longitudinal axis of the probe.

Cavitation is a void or bubble produced by the inability of the fluid to overcome the stresses induced by the motion of the probe. The collapse of the cavitation bubbles in and around cellular (or biological) material produces a shockwave that erodes or fragments the material allowing it to be removed through aspiration and suction. The mechanism of cavitation and its affect on tissues is well known in the art, and is described in such literature as U.S. Pat. No. 3,526,219 to Balamuth.

The equations of motion governing the operation of the are obtained by applying Newton's second law to the forces and accelerations acting upon an infinitesimal segment. The equation of motion for the transverse oscillations of a thin member (neglecting losses in the material and surroundings) is then given by:

$$\frac{\partial^4 \xi}{\partial X^4} + \frac{1}{(\kappa c)^2} \frac{\partial^2 \xi}{\partial t^2} = 0 \qquad 2.0$$

Where x is the distance along the flexible portion, t is the time in seconds $\xi$ is the transverse displacement, $\kappa$ is the radius of gyration, and c is the speed of sound in the material.

In can be shown for boundary conditions which assume a flexible member of length l fixed at one end and free at the other, the general solution to this equation will have the form:

$$\xi = \cos(\omega t + \phi_n)\left(A\left(\cosh\frac{\omega X}{v} - \cos\frac{\omega X}{v}\right) + B\left(\sinh\frac{\omega X}{v} - \sin\frac{\omega X}{v}\right)\right) \quad 2.1$$

Applying the boundary conditions it can be shown that $$\cot\left(\frac{\omega l}{2v}\right)\tanh\left(\frac{\omega l}{2v}\right) = 1 \quad 2.2$$

Where $\omega$ is the angular frequency in radians per second, x is the distance along the flexible member (as before) and v is the phase velocity given by:

$$v = \sqrt{\omega c \kappa} \quad 2.3$$

Here c is the longitudinal propagation velocity given by:

$$c = \sqrt{Y/\rho} \quad 2.4$$

where Y is Young's modulus and $\rho$ is the density of the material.

The solutions of equations 2.2 only occur at discrete frequencies, which for the first four overtones can be shown to be:

$$f_n = \frac{\pi c \kappa A_n}{8l^2} \quad 2.5$$

The $A_n$ terms are the solutions to equation 2.2. For the nth overtone they are $(1.194)^2, (2.988)^2, (5)^2, (7)^2 \ldots (2n-1)^2$ For overtones of the fundamental the node positions along the flexible member can be derived from the general solution given in equation 2.1 The nodal positions are the points at which the displacements and the bending moment are zero:

$$\xi_n = 0, \frac{\partial^2 \xi_n}{\partial X^2} = 0$$

with $$\frac{\partial^2 \xi_n}{\partial X^2} = \cos(\omega t + \phi)\left(\frac{\omega}{v}\right)^2\left(A\left(\cosh\frac{\omega X}{v} + \cos\frac{\omega X}{v}\right) + B\left(\sinh\frac{\omega X}{v} + \sin\frac{\omega X}{v}\right)\right) \quad 2.6$$

Using equations 2.1 and 2.6 it can be shown that:

$$\tan\frac{\omega X}{v} = \tanh\frac{\omega X}{v} \quad 2.7$$

which has solutions for:

$$\frac{\omega}{v} = \frac{\pi}{2l}(5, 7, 9 \ldots) \quad 2.8$$

The positions of the nodes for a member of length 1 will then be:
First overtone: x=0
Second overtone x=0, x=0.7741
Third overtone x=0, x=0.51, x=0.8681
Fourth overtone x=0, x=0.3561, x=0.6441, x=0.9051
Etc.

Figure Two shows the flexible portion oscillating in modes up to the fourth overtone.

For a practical design the forces acting on the flexible member have to be kept within safe limits for the material chosen. The bending moment of the flexible member is given by the equation:

$$M = YA\kappa^2 \frac{\partial^2 \xi}{\partial x^2} \quad 3.0$$

with A being the cross sectional area of the flexible member. Equation 3.0 will be recognized immediately as the standard differential equation for a beam in flexure.

The shear force acting along the member will be given by the equation:

$$F_s = \frac{\partial M}{\partial x} = YA\kappa^2 \frac{\partial^3 \xi}{\partial x^3} \quad 3.1$$

The preferred embodiment is a probe of circular cross section as described; however alternate shapes could be used as long as certain design constraints are considered. The key parameter is the $Y\kappa^2$ term appearing in equations 3.0 and 3.1, often referred to as the flexural stiffness. For annealed Ti-6AL-4V titanium optimal values are in the range $2.5 \times 10^7$ to $8.5 \times 10^7$ N/m. Note that the use of the flexural stiffness as a design parameter allows a shape independent specification for flexible member.

The driver and transformer sections are designed to provide sufficient longitudinal amplitude to support the desired transverse mode amplitude (see section on design constraints below). Typically the handle and probe assembly are designed to support a longitudinal amplitude which will be sufficient to induce buckling in the flexible member. The length of the entire probe and handle assembly is chosen to place a longitudinal anti-node at the end of the flexible member. This restricts the length of the handle and tip assembly to integer multiples of one half the longitudinal wavelength. In actual practice it has been found that a slight de-tuning of around 3 to 5 percent aids the conversion to the transverse mode. It should be noted that there is no longitudinal vibration of the tip as this is converted entirely into a transverse vibration through buckling of the thin member at the tip.

The force, or longitudinal push, imparted to the flexible member by the longitudinal section must be sufficient to induce buckling. The maximum longitudinal force exerted at startup must meet the Euler conditions for buckling, which are the solutions to equation 3.0, yielding the formula for the critical force:

$$P_{crit} = \frac{n^2\pi^2 Y\kappa^2}{l^2}, (n = 1, 2, 3 \ldots) \qquad 3.2$$

For the longitudinal drive the maximum stress at startup will be:

$$s = \frac{2\pi Y f \xi_m}{c} \qquad 3.3$$

Where $\xi_m$ is the maximum longitudinal displacement of the assembly (probe and handle), f is the drive frequency, c is the longitudinal propagation velocity (Eq. 2.4) and Y is Young's modulus for the material.

An optimal design will try to place as many anti-nodes as possible along the length of the flexible member. In the exemplary embodiment described and illustrated before, with a 3.748 inch long flexible member with a diameter of 0.020 inches, 6 nodes are produced at a frequency of 20 kHz.

The proceeding equations show that the stresses on the material increase with frequency. When coupled with the need to produce sufficient amplitude to remove tissue upper bounds for frequency can be established. To produce cavitation in fluid the transverse amplitude should be at least 75 microns. This will limit the frequency to about 80 kHz for 6Al-4V titanium (this disregards material losses which must be experimentally determined). The lower limit for the frequency is usually chosen to be outside of the range of human hearing, or greater than 20 kHz.

The transverse mode probe is much more effective at tissue removal than are the longitudinal designs of the prior art. One reason for this is because the action of the energy is along most of the length of the exposed flexible member and is not confined to the surface area of the tip of the member. The probes described in the prior art which are only driven in the longitudinal direction only work at the tip. Even with a solid tip, its active area in contact with tissue is much less than the transverse mode tip. Also, the tissue destruction of the transverse mode probes extends up to 1 mm circumferentially beyond the probe. The following calculations indicate the efficacy of the transverse mode compared to a standard longitudinal probe.

A rigid, solid, 4 mm probe works only at the tip. As it moves forward and back, it cavitates the fluid in front of it. The volume of tissue effected is:

| Frequency | f | 20,000 hz | |
|---|---|---|---|
| Stroke | Δx | 350 microns (.35 mm) | |
| Radius | r | 2 mm | |
| Cross sectional area | $A_x$ | $\pi r^2$ | 12.6 mm$^2$ |
| Volume of tissue removed per stroke | V | $A_x$*Δx | 4.40 mm$^3$ |
| Volume of tissue removed per time | $V_t$ | V*f/60/1,000 | 1.47 cc/min |

For a 2 cm long by 0.5 mm diameter probe working in the transverse mode:

| Frequency | f | 20,000 hz | |
|---|---|---|---|
| Radius | r | 0.25 mm | |
| Effective radius | $r_e$ | 1.25 mm | |
| Effective length | L | 20 mm | |
| Cross sectional area | $A_x$ | $\pi r_e^2$ | 4.91 mm$^2$ |
| Volume of tissue removed per stroke | V | $A_x$* L | 98.1 mm$^3$ |
| Volume of tissue removed per time | $V_t$ | V*f/60/1,000 | 32.7 cc/min |

This means that in these circumstances, the transverse mode tip removes tissue at a rate 22.2 times faster than the solid tip working in the longitudinal mode. Also, the transverse mode flexible member is typically ⅛$^{th}$ the size of the longitudinal probe. Comparing two, 0.5 mm probes, one working in the longitudinal mode and one in the transverse mode, the transverse mode tip removes tissue 1,428 times faster than the longitudinal probe.

The transverse mode probe is capable of maintaining its vibration when bent if the sum of the stresses imposed by the transverse vibration and the bending stresses do not exceed the elastic limit of the material. This offers significant advantages over longitudinal mode designs that are typically rigid over their entire length.

What is claimed is:

1. An ultrasonic device comprising:
a flexible probe coupled to a horn, the flexible probe having a proximal end, a distal end and a longitudinal axis therebetween, the flexible probe comprising first and second transformer sections configured to amplify an amplitude of longitudinal vibration when longitudinal vibration is applied to the transformer sections by the horn, the first transformer section having a first diameter and the second transformer section having a second diameter, the first diameter differing from the second diameter, wherein a portion of the flexible probe extending distally from the transformer sections has a degree of stiffness which allows the portion of the flexible probe extending distally from the transformer sections to support a transverse ultrasonic vibration when longitudinal vibration is applied by the transformer sections to the portion of the flexible probe extending distally from the transformer sections, and a length and a cross section of the portion of the flexible probe extending distally from the transformer sections are sized to support the transverse ultrasonic vibration with a plurality of transverse nodes and transverse anti-nodes along the length of the portion of the flexible probe extending distally from the transformer sections.

2. The device of claim 1 wherein the cross section of the flexible probe has a small profile.

3. The device of claim 1 wherein the cross section of the flexible probe is approximately circular.

4. The device of claim 1 wherein the transverse anti-nodes are points of a maximum transverse displacement along at least a portion of the longitudinal axis of the flexible probe.

5. The device of claim 1 wherein, during use, the transverse anti-nodes cause a cavitation in a fluid containing medium in communication with the flexible probe in a direction approximately perpendicular to the longitudinal axis of the flexible probe.

6. The device of claim 1 wherein the transformer sections are located between the proximal end of the flexible probe and the distal end of the flexible probe.

7. The device of claim 1, further comprising a driver coupled to the horn, the driver configured to produce longitudinal vibration.

8. The device of claim 1, wherein the longitudinal vibration applied to the transformer sections has a frequency in the range of about 20 kHz to about 80 kHz.

9. The device of claim 1, wherein the portion of the flexible probe extending distally from the transformer sections has a length such that eight transverse nodes are produced along the length of the portion of the flexible probe extending distally from the transformer sections when the longitudinal vibration is applied by the transformer sections to the portion of the flexible probe extending distally from the transformer sections.

10. The device of claim 1, wherein the portion of the flexible probe extending distally from the transformer sections comprises titanium.

11. The device of claim 1, wherein the transformer sections are sized to produce a gain of about 4-5 over the horn.

12. The device of claim 1, wherein the portion of the flexible probe extending distally from the transformer sections has a diameter of less than about 1 millimeter.

13. The device of claim 1, wherein the portion of the flexible probe extending distally from the transformer sections has a diameter of about 0.020 inches.

14. The device of claim 1, wherein the flexural stiffness of the portion of the flexible probe extending distally from the transformer sections is in the range of about $2.5 \times 10^7$ N/m to about $8.5 \times 10^7$ N/m.

15. The device of claim 1, wherein the first transformer section comprises a threaded portion and the horn comprises a threaded portion, the threaded portion of the first transformer section configured to mate with the threaded portion of the horn.

16. The device of claim 1, further comprising a sheath, the flexible probe being disposed within the sheath.

17. An ultrasonic medical device comprising:
an ultrasonic probe coupled to an ultrasonic horn, the ultrasonic probe having a proximal end, a distal end and a longitudinal axis therebetween, the ultrasonic probe comprising first and second transformer sections located between the proximal end of the ultrasonic probe and the distal end of the ultrasonic probe, the transformer sections configured to amplify an amplitude of longitudinal vibration when longitudinal vibration is applied to the transformer sections by the ultrasonic horn, the first transformer section having a first diameter and the second transformer section having a second diameter, the first diameter differing from the second diameter, a portion of the ultrasonic probe extending distally from the transformer sections being configured to vibrate in a direction transverse to the longitudinal axis of the ultrasonic probe when longitudinal vibration is applied by the transformer sections to the portion of the flexible probe extending distally from the transformer sections.

18. The device of claim 17 wherein the cross section of the ultrasonic probe has a small profile.

19. The device of claim 17 wherein the cross section of the ultrasonic probe is approximately circular.

20. The device of claim 17 wherein, during use, a transverse ultrasonic vibration along at least a portion of the longitudinal axis of the ultrasonic probe produces a plurality of transverse nodes and transverse anti-nodes along at least a portion of the longitudinal axis of the ultrasonic probe.

21. The device of claim 20 wherein the transverse antinodes are points of maximum transverse displacement along at least a portion of the longitudinal axis of the ultrasonic probe.

22. The device of claim 20 wherein, during use, the transverse anti-nodes cause a cavitation in a fluid containing medium in communication with the ultrasonic probe in a direction approximately perpendicular to the longitudinal axis of the ultrasonic probe.

23. The device of claim 20 wherein, during use, more than one of the plurality of transverse antinodes is in communication with a biological material.

24. The device of claim 17, further comprising an ultrasonic driver coupled to the horn, the ultrasonic driver configured to produce longitudinal ultrasonic vibration.

25. The device of claim 17, wherein the longitudinal vibration applied to the transformer sections has a frequency in the range of about 20 kHz to about 80 kHz.

26. The device of claim 17, wherein the portion of the ultrasonic probe extending distally from the transformer sections has a length such that eight transverse nodes are produced along length of the portion of the ultrasonic probe extending distally from the transformer sections when the longitudinal vibration is applied by the transformer sections to the portion of the ultrasonic probe extending distally from the transformer sections.

27. The device of claim 17, wherein the portion of the ultrasonic probe extending distally from the transformer sections comprises titanium.

28. The device of claim 17, wherein the transformer sections are sized to produce a gain of about 4-5 over the horn.

29. The device of claim 17, wherein the portion of the ultrasonic probe extending distally from the transformer sections has a diameter of less than about 1 millimeter.

30. The device of claim 17, wherein the portion of the ultrasonic probe extending distally from the transformer sections has a diameter of about 0.020 inches.

31. The device of claim 17, wherein the flexural stiffness of the portion of the ultrasonic probe extending distally from the transformer sections is in the range of about $2.5 \times 10^7$ N/m to about $8.5 \times 10^7$ N/m.

32. The device of claim 17, wherein the first transformer section comprises a threaded portion and the horn comprises a threaded portion, the threaded portion of the first transformer section configured to mate with the threaded portion of the horn.

33. The device of claim 17, further comprising a sheath, the ultrasonic probe being disposed within the sheath.

34. An ultrasonic medical device comprising:
a flexible probe coupled to a horn, the flexible probe having a proximal end, a distal end and a longitudinal axis therebetween;
a largest diameter of the flexible probe at a proximal end of the flexible probe;
a smallest diameter of the flexible probe at a distal end of the flexible probe; and
first and second transformer sections located between the proximal end of the flexible probe and the distal end of the flexible probe, the transformer sections configured to amplify an amplitude of longitudinal vibration when longitudinal vibration is applied to the transformer section by the horn, the first transformer section having a first diameter and the second transformer section having a second diameter, the first diameter differing from the second diameter,
wherein, when longitudinal vibration is applied by the transformer sections to a portion the flexible probe extending distally from the transformer sections, a transverse ultrasonic vibration is produced along the longitudinal axis of the portion of the flexible probe extending distally from the transformer sections, which produces a plurality of transverse nodes and transverse anti-nodes along the longitudinal axis of the portion of the flexible probe extending distally from the transformer sections.

35. The device of claim 34 wherein the cross section of the flexible probe has a small profile.

36. The device of claim 34 wherein the cross section of the flexible probe is approximately circular.

37. The device of claim 34 wherein the flexible probe is configured to vibrate in a direction transverse to at least a portion of the longitudinal axis of the flexible probe.

38. The device of claim 34 wherein the transverse anti-nodes are points of a maximum transverse displacement along at least a portion of the longitudinal axis of the flexible probe.

39. The device of claim 34 wherein, during use, the transverse anti-nodes cause a cavitation in a fluid containing medium in communication with the flexible probe in a direction approximately perpendicular to the longitudinal axis of the flexible probe.

40. The device of claim 34 wherein, during use, more than one of the plurality of transverse antinodes are in communication with a biological material.

41. The device of claim 34, further comprising a driver coupled to the horn, the driver configured to produce longitudinal vibration.

42. The device of claim 34, wherein the longitudinal vibration applied to the transformer sections has a frequency in the range of about 20 kHz to about 80 kHz.

43. The device of claim 34, wherein the portion of the flexible probe extending distally from the transformer sections has a length such that eight transverse nodes are produced along the length of the portion of the flexible probe extending distally from the transformer sections when the longitudinal vibration is applied by the transformer sections to the portion of the flexible probe extending distally from the transformer sections.

44. The device of claim 34, wherein the portion of the flexible probe extending distally from the transformer sections comprises titanium.

45. The device of claim 34, wherein the transformer sections are sized to produce a gain of about 4-5 over the horn.

46. The device of claim 34, wherein the portion of the flexible probe extending distally from the transformer sections has a diameter of less than about 1 millimeter.

47. The device of claim 34, wherein the portion of the flexible probe extending distally from the transformer sections has a diameter of about 0.020 inches.

48. The device of claim 34, wherein the flexural stiffness of the portion of the flexible probe extending distally from the transformer sections is in the range of about $2.5 \times 10^7$ N/m to about $8.5 \times 10^7$ N/m.

49. The device of claim 34, wherein the first transformer section comprises a threaded portion and the horn comprises a threaded portion, the threaded portion of the first transformer section configured to mate with the threaded portion of the horn.

50. The device of claim 34, further comprising a sheath, the flexible probe being disposed within the sheath.

* * * * *

UNITED STATES PATENT AND TRADEMARK OFFICE
CERTIFICATE OF CORRECTION

PATENT NO. : 7,494,468 B2  Page 1 of 1
APPLICATION NO. : 10/371781
DATED : February 24, 2009
INVENTOR(S) : Rabiner et al.

It is certified that error appears in the above-identified patent and that said Letters Patent is hereby corrected as shown below:

Title Page, Item (75) Inventors:
  delete "Robert A. Rabiner, Chelmsford, MA (US)" and replace with --Robert A. Rabiner, North Reading, MA (US)--.

Claim 26, column 10, line 16:
  after "along" insert --the--.

Claim 34, column 10, line 56-57:
  delete "section" and replace with --sections--.

Signed and Sealed this

Fifth Day of May, 2009

JOHN DOLL
*Acting Director of the United States Patent and Trademark Office*